United States Patent
Griffiths

(10) Patent No.: US 9,861,666 B2
(45) Date of Patent: Jan. 9, 2018

(54) ANTIVIRAL METHODS AND COMPOSITIONS COMPRISING PROBIOTIC BACTERIAL MOLECULES

(71) Applicant: Mansel Griffiths, Rockwood (CA)

(72) Inventor: Mansel Griffiths, Rockwood (CA)

(*) Notice: Subject to any disclaimer, the term of this patent is extended or adjusted under 35 U.S.C. 154(b) by 0 days.

(21) Appl. No.: 14/457,916

(22) Filed: Aug. 12, 2014

(65) Prior Publication Data
US 2015/0044188 A1 Feb. 12, 2015

Related U.S. Application Data

(60) Provisional application No. 61/865,066, filed on Aug. 12, 2013.

(51) Int. Cl.
| | |
|---|---|
| *A61K 35/74* | (2015.01) |
| *A61K 38/07* | (2006.01) |
| *A61K 38/08* | (2006.01) |
| *A61K 35/747* | (2015.01) |
| *A61K 47/26* | (2006.01) |
| *A61K 45/06* | (2006.01) |
| *A61K 35/741* | (2015.01) |
| *A61K 9/19* | (2006.01) |
| *A23L 33/135* | (2016.01) |

(52) U.S. Cl.
CPC .......... *A61K 35/747* (2013.01); *A23L 33/135* (2016.08); *A61K 9/19* (2013.01); *A61K 35/741* (2013.01); *A61K 38/07* (2013.01); *A61K 38/08* (2013.01); *A61K 45/06* (2013.01); *A61K 47/26* (2013.01); *A23V 2002/00* (2013.01)

(58) Field of Classification Search
None
See application file for complete search history.

(56) References Cited

FOREIGN PATENT DOCUMENTS

| CA | WO 2009155711 A1 * | 12/2009 | ............. A23K 1/009 |
| CH | WO 2009118243 A1 * | 10/2009 | ........... A23L 1/3014 |

OTHER PUBLICATIONS

Botic et al., "A novel eukaryotic cell culture model to study antiviral activity of potential probiotic bacteria", International Journal of Food Microbiology 2007, vol. 115, pp. 227-234.*
Cadieux et al. "Lactobacillus Strains and Vaginal Ecology", *JAMA* 287(15):1940-1941.
Choi et al. "Antiviral Activity of Yogurt against Enterovirus 71 in Vero Cells", *Food. Sci. Biotechnol.* 19(2):289-295 (2010).
Medellin-Pena et al. "Effect of Molecules Secreted by *Lactobacillus acidophilus* Strain La-5 on *Escherichia coli* O157:H7 Colonization", *Applied and Environmental Microbiology* 75(4):1165-1172 (2009).
Rao et al. "Toward a live microbial microbicide for HIV: Commensal bacteria secreting an HIV fusion inhibitor peptide", *Proc. Natl. Acad. Sci.* 102(34):11993-11998 (2005).
Torres et al. "Safety, formulation, and in vitro antiviral activity of the antimicrobial peptide subtilosin against herpes simplex virus type 1", *Probiotics Antimicrob Proteins.* 5(1):26-35.
Notification of Transmittal of the International Search Report and the Written Opinion of the International Searching Authority, or the Declaration corresponding to International Application No. PCT/CA2014/000618 dated Nov. 12, 2014.

* cited by examiner

*Primary Examiner* — Michelle F Paguio Frising
(74) *Attorney, Agent, or Firm* — Myers Bigel, P.A.

(57) ABSTRACT

Molecules secreted or derived from probiotic bacteria are provided for use in compositions and methods for the treatment and/or prevention of infection by pathogenic viruses. The isolated secreted molecules can also be used in nutritional or medical food products which provide probiotics to the gastrointestinal tract of a mammal.

24 Claims, 22 Drawing Sheets

ANTIVIRAL METHODS AND COMPOSITIONS COMPRISING PROBIOTIC BACTERIAL MOLECULES

RELATED APPLICATION

This application claims priority to U.S. Provisional Application No. 61/865,066, filed on Aug. 12, 2013. The content of this application is incorporated herein by reference in its entirety.

FIELD OF THE INVENTION

This invention relates generally to the control of pathogenic viruses in mammals. More particularly, the invention relates to the isolation and identification of molecules secreted/derived from probiotic bacteria for use in compositions and methods for the treatment and/or prevention of infection by pathogenic viruses.

BACKGROUND OF THE INVENTION

Norovirus is a genus of genetically diverse single-stranded RNA, non-enveloped viruses in the Caliciviridae family. The known viruses in the genus are all considered to be the strains of a single species called Norwalk virus. The viruses are transmitted by fecally contaminated food or water; by person-to-person contact; and via aerosolization of the virus and subsequent contamination of surfaces. Noroviruses are the most common cause of viral gastroenteritis in humans, and affect people of all ages.

Probiotic bacteria are known to stimulate the immune system and exert a competitive exclusion of pathogenic and putrefactive bacteria, reduce the amounts of ammonia and cholesterol in the blood, and promote absorption of minerals (50). Additionally, probiotic bacteria produce antagonist effects against pathogenic microorganisms; stimulate the immune system; improve lactose digestion; are lipolytic, thereby allowing fats to be more digestible; reduce plasma cholesterol; protect the intestinal mucosa, thereby assuring effective assimilation of the nutritive substances; produce polysaccharides that are active on some tumors; and reduce viability of some enzyme-producing microorganisms which catalyze the conversion of procarcinogenic substances into carcinogenic substances. It is believed that the probiotic bacteria exert their effects in a synergistic manner to curtail and retard the growth of pathogenic and detrimental bacteria of the gut (51 and 52).

It is believed that the health and well being of people and animals can be positively or negatively influenced by the microorganisms which inhabit the gastrointestinal tract, and in particular the large bowel. These microorganisms through the production of toxins, metabolic by-products, short chain fatty acids, and the like affect the physiological condition of the host and improve the physiological well being of the host. As a result, research has focused on using probiotic cultures in a variety of compositions and methods to improve health.

For example, US 20040161422 discloses a nutritional food product comprising at least one probiotic bacteria to improve gut function. U.S. 20040115177 discloses methods of administering probiotic bacteria to livestock animals in an amount effective to reduce the amount of hazardous bacteria. Dietary supplements such as those for example sold as part of the PARINAT™ line is formulated with *Lactobacillus acidophilus* strain L.B. and is stated to be beneficial for general digestive and intestinal problems.

US 20110262400 (incorporated herein by reference in its entirety) describes the use of certain secreted molecules isolated from probiotic bacteria for treating or preventing infection by harmful enteric pathogens in mammals, such as *Escherichia coli* O157:H7 and *Salmonella*.

In view of the foregoing, it would be desirous to isolate and characterize the factor(s) produced by probiotic bacteria that provide beneficial effects in mammals for prophylaxis, prevention and treatment of harmful viral infection as well as use of such molecules as nutritional and food supplements for general health.

SUMMARY OF THE INVENTION

Molecules secreted/derived from probiotic bacteria and their use in treating, preventing, inhibiting, or ameliorating viral infections are described herein. The molecules are secreted/derived from probiotic bacteria meaning that they are secreted by probiotic bacteria directly into the medium or derived from culture fractions.

Thus, also provided are isolated probiotic proteinaceous fractions from probiotic bacteria and the novel molecules isolated from such fractions. Described herein is the isolation, characterization and methods of use of the probiotic molecules to prevent or treat infection by harmful viruses as an alternative or adjunct to traditional antiviral therapy. The molecules described herein can be used or ingested to improve health and incorporated into beverage and food sources to improve nutritional qualities.

The molecules described herein are low molecular weight and in aspects, proteinaceous as well as heat-stable and partially affected by enzymatic treatment. The secreted molecules described herein can also be used as a nutritional supplement to help maintain and/or increase the general health of a mammal and may be incorporated into a variety of food and beverage products for ease of ingestion as well as incorporated into medicaments. As such the secreted molecules described herein can be regarded in one aspect as probiotic. By "probiotic" it is generally defined as a live microbial food supplement which beneficially affects the host human or animal by improving its intestinal microbial balance. However, as used herein, "probiotic" is meant to encompass the secreted molecules from probiotic bacteria.

According to an aspect, isolated secreted molecules from probiotic bacteria are provided, said secreted molecules being effective in vitro and in vivo to prevent and/or treat viral infection.

According to an aspect, isolated secreted molecules from probiotic bacteria are provided, said secreted molecules being effective for mammalian nutritional health.

According to another aspect, compositions comprising lyophilized probiotic proteinaceous fractions are provided as effective in the prevention and/or treatment of infection by harmful viruses. Such lyophillized fractions may also be used as a source of mammalian nutritional health.

According to another aspect, isolated secreted molecules from a probiotic bacteria selected from *Lactobacillus*, *Bifidobacteria*, and *Streptococcus* are provided. In aspects, the *Bifidobacteria* is a species selected from *Bifidobacterium longum*, *Bifidobacterium bifidum*, *Bifidobacterium infantis* *Bifidobacterium crudilactis*. In other aspects, the probiotic bacteria is a *Lactobacillus* selected from *Lactobacillus acidophilus* (La-5), *Lactobacillus fermentum*, *Lactobacillus rhamnosus*, *Lactobacillus helveticus*, *Lactobacillus plantarum*, *Lactobacillus helveticus*, and *Lactobacillus plantarum*. In other aspects the bacterium is *Lactococcus Lactis*. Still in other aspects the probiotic bacteria is from a *Streptococcus* such as *Streptococcus thermophilus*.

According to another aspect, the secreted molecules described herein are effective for treatment and prophylactic therapy against infectious viruses, such as but not limited to members of the Caliciviridae family, such as the Norovirus genus, including the species called Norwalk virus.

According to another aspect, there is provided a composition comprising one or more secreted molecules from a probiotic bacterium, said composition being effective to reduce and/or prevent harmful viral infection in mammals.

According to another aspect, there is provided a composition comprising one or more secreted molecules from a probiotic bacterium and an antiviral, said composition being effective to reduce and/or prevent harmful viral infection in mammals.

According to another aspect, there is provided a composition comprising one or more secreted molecules from a probiotic bacterium, a sugar source and optionally an antiviral, said composition being effective to reduce and/or prevent harmful viral infection in mammals. In aspects, the sugar source comprises glucose.

According to another aspect, there is provided is a composition comprising one or more secreted molecules from a bacteria selected from *Lactobacillus*, *Bifidobacterium* and *Streptococcus* and mixtures thereof.

In aspects, the secreted molecules are proteinaceous. In further aspects, the secreted molecules are small, low molecular weight peptides. In further aspects, the secreted molecules can withstand heating at up to about 90° C., freezing, thawing, lyophilization and/or spray drying.

According to another aspect, there is provided a secreted molecule from *Lactobacillus acidophilus* (La-5), wherein said molecule comprises at least one of the following sequences: YPVEPF, YPPGGP, YPPG and NQPY.

According to another aspect, there is provided a composition comprising a secreted molecule from *Lactobacillus acidophilus* (La-5), wherein said molecule is effective against infectious viruses, such as but not limited to members of the Caliciviridae family, such as the Norovirus genus, including the species called Norwalk virus.

According to another aspect, there is provided a composition comprising a secreted molecule from *Lactobacillus acidophilus* (La-5), wherein said molecule comprises one of the following amino acid sequences: YPVEPF, YPPGGP, YPPG and NQPY and said molecule can prevent and/or treat viral infection, caused by viruses such as but not limited to members of the Caliciviridae family, such as the Norovirus genus, including the species called Norwalk virus. The amino acid sequences may have substitutions that do not adversely affect the activity of the secreted molecule.

According to another aspect, there is provided a composition comprising a secreted molecule from a *Bifidobacterium* selected from *Bifidobacterium longum*, *Bifidobacterium bifidum* and *Bifidobacterium infantis* and/or *Bifidobacterium crudilactis*, wherein said composition can prevent and/or treat infection by members of the Caliciviridae family, such as the Norovirus genus, including the species called Norwalk virus, in vivo in a mammal.

According to another aspect, there is provided a food product, beverage product, medicament or nutritional supplement that comprises one or more secreted molecules from a bacterium selected from *Lactobacillus acidophilus* (La-5), *Lactobacillus fermentum*, *Lactobacillus rhamnosus*, *Lactobacillus helveticus*, *Lactobacillus plantarum*, *Lactococcus Lactis*, *Streptococcus thermophilus*, *Bifidobacterium longum*, *Bifidobacterium bifidum*, *Bifidobacterium infantis*, *Bifidobacterium crudilactis*, *Streptococcus thermophilus* and combinations thereof.

According to another aspect, there is provided an ingestible health product for mammals, wherein said ingestible health product has probiotic characteristics and comprises one or more secreted molecules from *Lactobacillus acidophilus* (La-5), *Lactobacillus fermentum*, *Lactobacillus rhamnosus*, *Lactobacillus helveticus*, *Lactobacillus plantarum*, *Lactococcus Lactis*, *Streptococcus thermophilus*, *Bifidobacterium longum*, *Bifidobacterium bifidum* and *Bifidobacterium infantis* and/or *Bifidobacterium crudilactis*.

According to another aspect, there is provided a method for preventing and/or therapeutically treating viral infections, the method comprising administering to a subject an effective amount of a composition comprising one or more secreted molecules from *Lactobacillus acidophilus* (La-5). In aspects, the secreted molecules may further comprise those from *Lactobacillus fermentum*, *Lactobacillus rhamnosus*, *Lactobacillus helveticus*, *Lactobacillus plantarum*, *Lactococcus Lactis*, *Streptococcus thermophilus*, *Bifidobacterium longum*, *Bifidobacterium bifidum*, *Bifidobacterium infantis*, *Bifidobacterium crudilactis*, *Streptococcus thermophilus* and combinations thereof.

Also provided is a method for preventing the carriage by a food production animal of viral species that cause human disease. The method comprises the step of administering an effective amount of secreted molecules from probiotic bacteria to the food production animal prior to exposure to viral species that cause human disease. The administration of the secreted molecules from probiotic bacteria is accomplished by feeding a feed supplement or additive which comprises an effective amount of said secreted molecules, or by supplying a water treatment additive or inoculum to the animals' drinking water. Therefore, provided herein is a feed supplement composition comprising secreted molecules from probiotic bacteria and a water additive comprising secreted molecules from probiotic bacteria. The probiotic bacteria may be selected from the group consisting of *Lactobacillus acidophilus* (La-5), *Lactobacillus fermentum*, *Lactobacillus rhamnosus*, *Lactobacillus helveticus*, *Lactobacillus plantarum*, *Lactococcus Lactis*, *Streptococcus thermophilus*, *Bifidobacterium longum*, *Bifidobacterium bifidum*, *Bifidobacterium infantis*, *Bifidobacterium crudilactis*, *Streptococcus thermophilus* and combinations thereof.

According to another aspect, there is provided a method of preventing infection by harmful viruses in a mammal, the method comprising administration of an effective amount of a secreted molecule(s) from a probiotic bacteria selected from the group consisting of *Lactobacillus acidophilus* (La-5), *Lactobacillus fermentum*, *Lactobacillus rhamnosus*, *Lactobacillus helveticus*, *Lactobacillus plantarum*, *Lactococcus Lactis*, *Streptococcus thermophilus*, *Bifidobacterium longum*, *Bifidobacterium bifidum*, *Bifidobacterium infantis*, *Bifidobacterium crudilactis*, *Streptococcus thermophilus* and combinations thereof.

According to another aspect, there is provided a method of preventing viral infection in a mammal, the method comprising administration of an effective amount of a secreted molecule(s) from a probiotic bacteria selected from the group consisting of *Lactobacillus acidophilus* (La-5), *Lactobacillus fermentum*, *Lactobacillus rhamnosus*, *Lactobacillus helveticus*, *Lactobacillus plantarum*, *Lactococcus Lactis*, *Streptococcus thermophilus*, *Bifidobacterium longum*, *Bifidobacterium bifidum* and *Bifidobacterium infantis* and/or *Bifidobacterium crudilactis*.

According to another aspect, there is provided a method of improving the general health of a mammal, the method comprising administration of an effective amount of a secreted molecule(s) from a probiotic bacteria selected from the group consisting of *Lactobacillus acidophilus* (La-5), *Lactobacillus fermentum, Lactobacillus rhamnosus, Lactobacillus helveticus, Lactobacillus plantarum, Lactococcus Lactis, Streptococcus thermophilus, Bifidobacterium longum, Bifidobacterium bifidum* and *Bifidobacterium infantis* and/or *Bifidobacterium crudilactis*.

In any of the aforementioned methods, the molecule(s) may be provided isolated and/or purified or within a cell-free culture fraction from the probiotic bacteria. Alternatively, the secreted molecules may be provided within a composition, edible food product or supplement or ingestible liquid. They can be used in conjunction with whole probiotic bacteria and with pharmaceuticals such as known antivirals.

Additionally, whole probiotic bacteria that secrete the molecules may be used in a manner such that they will secrete the probiotic molecules in a therapeutically effective amount for use. For example, a yogurt composition comprising the whole probiotic bacteria may be used when the probiotic bacteria are cultured in the bacteria under conditions in which they will secret the molecules in a therapeutically effective amount into the yogurt composition.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

BRIEF DESCRIPTION OF THE DRAWINGS

The present invention will be further understood from the following description with reference to the drawings, in which.

*acidophilus* La-5 (La554356 NZ and Protrainer) on virus-free cell cultures. (B) Effect of mMRS medium alone (mmRS medium) or including probiotic peptides from *B. longum* (Blong Run) or two different strains of *L. acidophilus* La-5(La554356 and New La554356) .c virus-free cell cultures. The y-axis represents absorbance and the x-axis represents the various media concentrations that were tested.

Figure 18:
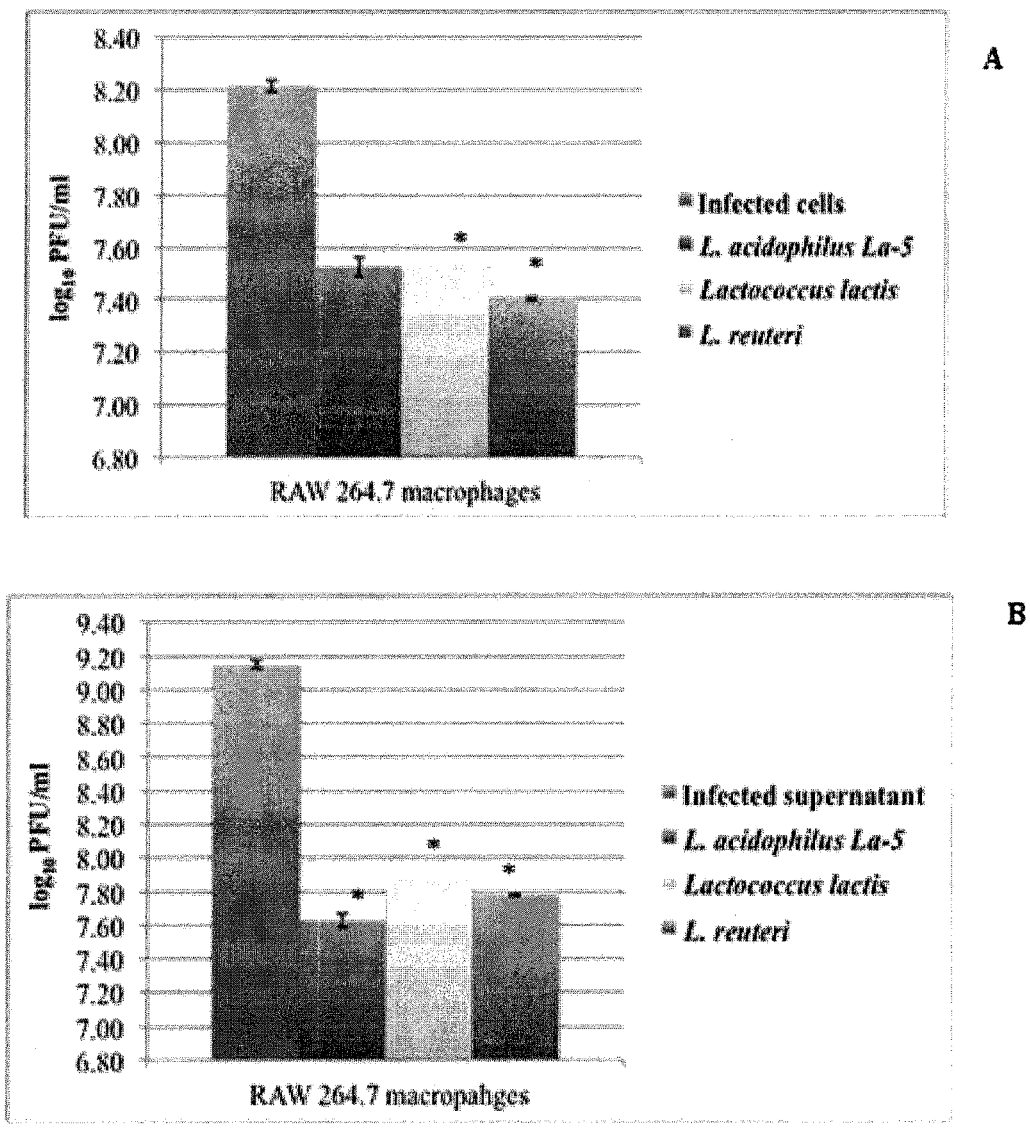

FIG. 18, (A) Effect of probiotic CFSM on murine norovirus infection of RAW 264.7cells. MNV-1 number in infected cells without probiotic CFSM and cells including probiotic peptides from *L acidophilus* La-5,*L lactis* and *L. reuteri*, are shown, from left to right respectively. (B) Effect of CFSM on MNV-1 number in medium. MNV-1 number in the supernatant of infected cells grown without probiotic CFSM, and in the supernatant of cells grown including probiotic peptides from *L. acidophilus* La-5. *L. lactis* and *L. reuteri*, are shown, from left to right respectively. Asterisks indicate statistical significance in the difference between the number MNV-1 particles in CFSM treated cells and media, and untreated cells and media.

FIG. 19. (A) Control monolayer cells infected with HAV. (B) Effect of probiotic CFSM derived from *L. acidophilus* La-5 on monolayer HAV-infected cell cultures. (C) Effect of probiotic CFSM derived from *L. reuteri* on monolayer HAV-infected cell cultures. (D) Effect of probiotic CFSM derived from *Lactococcus lactis* on monolayer HAV-infected cell cultures.

Figure 20:
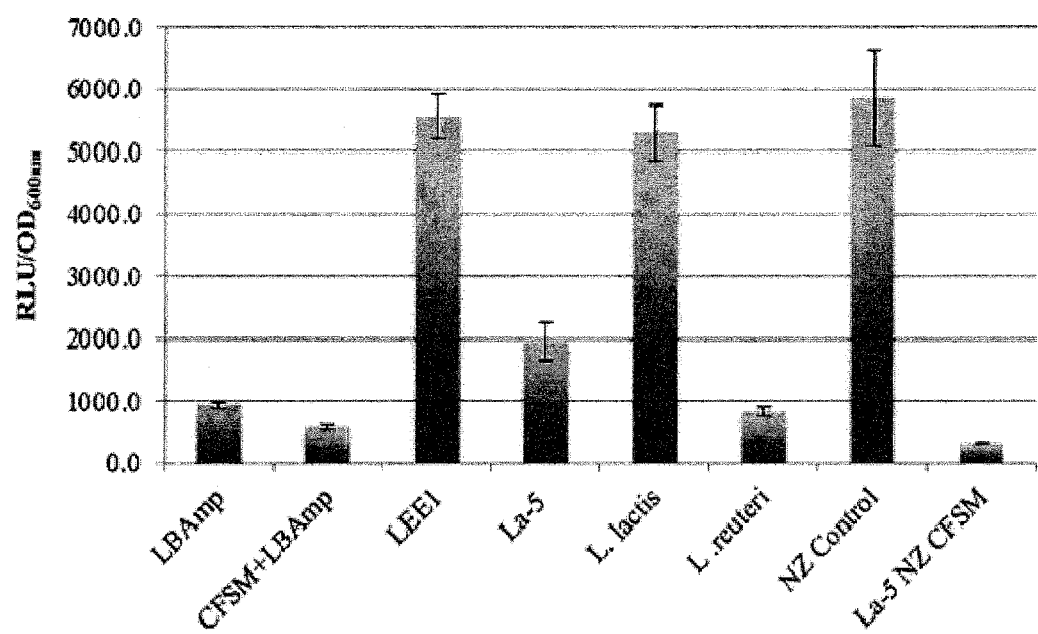

FIG. 20. Supernatant activity based on the downregulation of the LEE::luxCDABE *E. coli* O157 construct.

Figure 21:
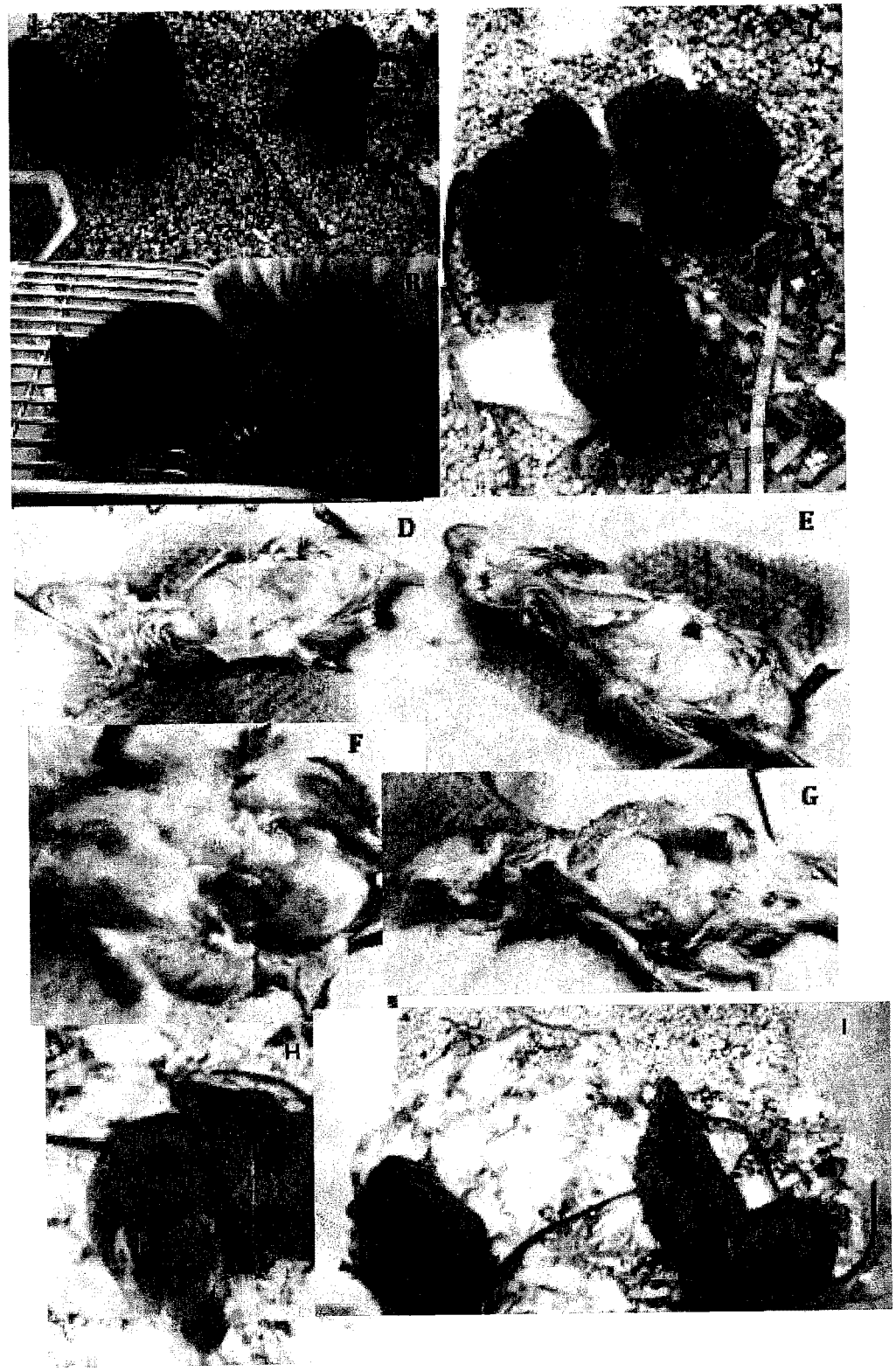

FIG. 21. (A) General well-being of mice treated with probiotic supernatant at 3d poi. (B) General well-being of mice treated with probiotic supernatant at 3d poi. (C) General well-being of untreated mice at 3d poi. (D) Internal organs of mice treated with La5 at 3d poi. (E) Internal organs of mice treated with La5 at 4d poi. (F) Internal organs of mice treated with lactis at 2d poi. (G) Internal organs of untreated mice. (H) General well-being of mice treated with lactis probiotic supernatant at the end of the trial. (I) General well-being of mice treated with La5 probiotic supernatant at the end of the trial.

DETAILED DESCRIPTION

The present invention provides secreted molecules isolated from probiotic bacteria and further culture fractions of the bacteria that can minimize, inhibit, treat, and/or prevent infection by harmful viruses in mammals, such as enteric viruses. The molecules are demonstrated to be effective both in vitro and in vivo. In particular, the molecule(s) have been isolated and characterized from *Lactobacillus acidophilus* (La-5) as well as from strains of *Bifidobacterium* such as but not limited to *Bifidobacterium longum, Bifidobacterium bifidum, Bifidobacterium infantis*, and *Bifidobacterium crudilactis*, and also from *Lactobacillus fermentum, Lactobacillus rhamnosus, Lactobacillus helveticus, Lactobacillus plantarum, Lactococcus Lactis*, and *Streptococcus thermophilus*. The secreted molecules are now shown effective against infection by viruses such as Norovirus.

Unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning. A Laboratory Manual, Cold Springs Harbor Press (Cold Springs Harbor, N.Y. 1989), each of which are incorporated herein by reference. For the purposes of the present invention, the following terms are defined below.

By "secreted/derived," it is meant that the probiotic bacteria secrete the novel molecules directly into the culture medium. In aspects, the molecules can also be formed indirectly within the culture medium.

"Variants" of the sequences described herein are biologically active sequences that have a peptide sequence that differs from the sequence of a native or wild-type sequence, by virtue of an insertion, deletion, modification and/or substitution of one or more amino acids within the native sequence. Such variants generally have less than 100% sequence identity with a native sequence. Ordinarily, however, a biologically active variant will have an amino acid sequence with at least about 70% sequence identity with the sequence of a corresponding naturally occurring sequence, typically at least about 75%, more typically at least about 80%, even more typically at least about 85%, even more typically at least about 90%, and even more typically of at least about 95%, 96%, 97%, 98%, or 99% sequence identity. The variants nucleotide fragments of any length that retain a biological activity of the corresponding native sequence. Variants also include sequences wherein one or more amino acids are added at either end of, or within, a native sequence. Variants also include sequences where a number of amino acids are deleted and optionally substituted by one or more different amino acids.

"Percent sequence identity" is defined herein as the percentage of amino acid residues in the candidate sequence that are identical with the residues in the sequence of interest after aligning the sequences and introducing gaps, if necessary, to achieve the maximum percent sequence identity, and not considering any conservative substitutions as part of the sequence identity. None of 5', 3', or internal extensions, deletions or insertions into the candidate sequence shall be construed as affecting sequence identity or homology. Methods and computer programs for the alignment are well known in the art, such as "BLAST".

"Active" or "activity" for the purposes herein refers to a biological activity of a native or naturally-occurring probiotic molecule, wherein "biological" activity refers to a biological function (either inhibitory or stimulatory) caused by a native or naturally-occurring probiotic molecule. Thus, "biologically active" or "biological activity" when used in conjunction with the probiotic molecules described herein refers to probiotic molecule or amino acid sequence that exhibits or shares an effector function of the native probiotic molecule or sequence. For example, the probiotic molecules described herein have the biological activity of preventing, inhibiting, or treating an enteric viral infection in an animal.

"Biologically active" or "biological activity" when used in conjunction with variant sequences means that the variant sequences exhibit or share an effector function of the parent sequence. The biological activity of the variant sequence may be increased, decreased, or at the same level as compared with the parent sequence.

"Isolated" refers to a molecule that has been purified from its source or has been prepared by recombinant or synthetic methods and purified. Purified probiotic molecules are substantially free of other amino acids.

"Substantially free" herein means less than about 5%, typically less than about 2%, more typically less than about 1%, even more typically less than about 0.5%, most typically less than about 0.1% contamination with other source amino acids. An "essentially pure" probiotic molecule composition means a composition comprising at least about 90% by weight of the probiotic molecule, based on total weight of the composition, typically at least about 95% by weight, more typically at least about 90% by weight, even more typically at least about 95% by weight, and even more typically at least about 99% by weight of nucleotide, based on total weight of the composition.

As used herein, "treatment" or "therapy" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of cellular degeneration or damage, such as due to viral infection, or may render the cells more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat a viral infection. Effective amounts of the agents described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The agents of the present invention may, in aspects, be administered before, during or after treatment with conventional therapies for the disease or disorder in question, such as a viral infection.

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers that are non-toxic to the cell or mammal being exposed thereto at the dosages and concentrations employed. Often the pharmaceutically acceptable carrier is an aqueous pH buffered solution. Examples of pharmacologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, and dextrins; chelating agents such as EDTA; sugar alcohols such as mannitol and sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of a drug to a subject, such as a mammal. The components of the liposome are commonly arranged in a bilayer formation, similar to the lipid arrangement of biological membranes.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component or sequence defined herein as being included may be explicitly excluded from the claimed invention by way of proviso or negative limitation. Similarly, the subject or patient to be treated may be defined as having or not having any of the symptoms or outcomes of sepsis described herein or known to a skilled person.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The novel secreted molecules described herein in aspects are small peptides that are temperature resistant (can be heated, frozen and thawed and still exhibit activity), are stable for long periods of time frozen (over two years), can be produced readily in large volumes (for example about 2 mg/L), can be lyophilized and spray dried. The molecules can be incorporated into a variety of substances for administration to a mammal such as any type of animal and humans. For example, the secreted molecules can be incorporated into any type of food product, nutritional supplement or beverage for animal or human consumption.

As a therapeutic, the secreted molecules described herein can be administered in a manner to an animal or human for the effective treatment of viral infection such as by Norovirus. As a therapeutic or prophylactic, the treatment can be in conjunction with other antivirals or other therapies as is desired. In another embodiment, the secreted molecules described herein can be used in compositions and in methods in addition to use of whole probiotic bacteria. Alternatively, whole probiotic bacteria can be used alone, provided the bacteria are cultured and/or used such that they secrete the molecules into the culture medium in a therapeutically effective amount.

In aspects the secreted molecules are isolated from *Lactobacillus acidophilus* (La-5), wherein said molecule comprises one or more of the following amino acid sequences: YPVEPF, YPPGGP, YPPG and NQPY. It is understood by one of skill in the art that these sequences can be altered by deletion, substitution or insertion so long as the activity of the secreted molecules is not substantially affected to reduce and/or prevent viral infection.

The sequences can further have insertions, substitutions, or deletions of one or more of the amino acid residues. Furthermore, the molecules described herein may further be altered with glycosylation, unglycosylation, organic and inorganic salts and covalently modified. Also encompassed are molecules modified to increase in vivo half life, e.g., PEGylated. Possible but non-limiting modifications to the molecules described herein include modifications comprising combinations of amino acid substitutions together with a deletion of one or more amino acids or the addition of one or more amino acids.

In a generalized aspect, the molecules described herein can be provided in a therapeutically effective amount alone or within a composition and in amounts that may vary according to factors such as the infection state/health, age, sex, and weight of the recipient. Dosage regimes may be adjusted to provide the optimum therapeutic response and may be at the discretion of the attending physician or veterinarian. For example, several divided doses may be administered daily or on at periodic intervals, and/or the dose may be proportionally reduced as indicated by the exigencies of the therapeutic situation. The amount of the molecule for administration will depend on the route of administration, time of administration and may be varied in accordance with individual subject responses. Suitable administration routes are, for example, intramuscular injections, subcutaneous injections, intravenous injections or intraperitoneal injections, oral and intranasal administration. Compositions comprising the molecules or the culture fractions described herein may comprise about 0.1% to about 99% by weight of the active and any range there-in-between.

The molecules or culture fractions may be administered over a period of hours, days, weeks, or months, depending on several factors, including the severity of the infection being treated, whether a recurrence of the infection is considered likely, or to prevent infection, etc. The administration may be constant, e.g., constant infusion over a period of hours, days, weeks, months, etc. Alternatively, the administration may be intermittent, e.g., the molecules may be administered once a day over a period of days, once an hour over a period of hours, or any other such schedule as deemed suitable.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in "Handbook of Pharmaceutical Additives" (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456 (the entirety of which is incorporated herein by reference).

Pharmaceutically acceptable carriers are well known to those skilled in the art and include, for example, sterile saline, lactose, sucrose, calcium phosphate, gelatin, dextrin, agar, pectin, peanut oil, olive oil, sesame oil and water. Furthermore the pharmaceutical composition may comprise one or more stabilizers such as, for example, carbohydrates including sorbitol, mannitol, starch, sucrose, dextrin and glucose, proteins such as albumin or casein, and buffers like alkaline phosphates.

For example, in accordance with a veterinary aspect, a composition containing the secreted molecules in an acceptable carrier is administered to an animal at least about three weeks prior to shipment of the animal in an amount effective to reduce the amount of virus in the animal both before and after harvest. The secreted molecules from probiotic bacteria may be delivered in an acceptable carrier via a food route of administration (e.g., milk product, water, feed, or any suitable medium) or by a medicinal route of administration (e.g., oral or intranasal innoculation). Acceptable carriers for the secreted molecules from probiotic bacteria include feed products for the livestock animal, including, for example, milk or yogurt cultures. A dry form of the secreted molecules from probiotic culture can also be produced and added to feed by the process of lyophilization. Lyophillized secreted molecules may be delivered to animals by any suitable route of administration including via dry feed and water. By administering such therapy in advance of transport, significant levels of hazardous viruses are reduced in the livestock pre and post slaughter.

In another aspect, the probiotic molecules and/or the bacteria from which the probiotic molecules are secreted/derived may be incorporated into food sources or their packaging that may be susceptible to harboring viral pathogens. For example, common viruses transmitted by food include Hepatitis A virus, Norovirus, Rotavirus, Hepatitis E virus, Astrovirus, Reovirus, and Echovirus. These viruses may be found in, for example, meat and dairy products, produce, and even frozen fruit mixes. By incorporating the molecules and/or bacteria that produce the molecules into these foods or their packagings, their propagation may be reduced or inhibited, thereby reducing the incidence or likelihood of infection.

In another non-limiting aspect, administration of the isolated secreted molecules from probiotic bacteria can be accomplished by any method likely to introduce the molecules into the digestive tract, such as orally or rectally. The bacteria can be mixed with a carrier and applied to liquid or solid feed or to drinking water. The carrier material should be non-toxic to the animal. The molecules can also be formulated into a composition provided as an inoculant paste to be directly injected into an animal's mouth. The formulation can include added ingredients to improve palatability, improve shelf-life, impart nutritional benefits, and the like. If a reproducible and measured dose is desired, the molecules can be administered by a rumen cannula, as described herein. The amount of the secreted molecules isolated from probiotic bacteria to be administered is governed by factors affecting efficacy. By monitoring the numbers of viral particles in feces before, during and after administration of the secreted molecules from probiotic bacteria, those skilled in the art can readily ascertain the dosage level needed to reduce the amount of virus carried by the animals. The secreted molecules from one or more strains of probiotic bacteria can be administered together. A combination of strains can be advantageous because individual animals may differ as to the strain which is most persistent in a given individual.

The secreted molecules from probiotic bacteria can be administered as a preventative, to prevent animals not presently carrying a pathogenic virus from acquiring the strain by exposure to other animals or environments where the pathogenic virus is present. Young calves and mature animals about to be transferred to a new location, such as a feed lot, are attractive candidates for preventative administration. Treatment of animals carrying a pathogenic virus can be accomplished to reduce or eliminate the amount of pathogenic virus carried by the animals, by administering the secreted molecules from probiotic bacteria to virus-infected animals. Animals known to be shedding virus particles in feces, or those raised where a pathogenic viral strain is known to exist are also suitable candidates for treatment with the molecules described herein.

The methods for administering the secreted molecules from probiotic bacteria are essentially the same, whether for prevention or treatment. Therefore, the need to first determine whether a pathogenic virus is being carried by the animals is removed. By routinely administering an effective dose to all the animals of a herd, the risk of contamination by a pathogenic virus can be substantially reduced or eliminated by a combination of prevention and treatment.

It is understood by one of skill in the art that the isolated molecules and culture fractions containing such, can be used in conjunction with known antiviral therapies for prevention and/or treatment of bacterial infection in mammals. It is also understood that compositions of the novel molecules described herein, whether isolated or in isolated culture fraction, can also be used in conjunction (formulated with) with a sugar source such as for example glucose in amounts of up to about 0.01% to about 0.1% or more by weight of the composition.

It is also understood that although the compositions described herein may be directly ingested or used as an additive in conjunction with foods, it will be appreciated that they may be incorporated into a variety of foods and beverages including but not limited to yoghurts, ice creams, cheeses, baked products such as bread, biscuits and cakes, dairy and dairy substitute foods, confectionery products, edible oil compositions, spreads, breakfast cereals, juices, meats, produce, and the like. Within the scope of the term "foods" are to be included in particular food likely to be classified as functional foods, i.e. "foods that are similar in appearance to conventional foods and are intended to be consumed as part of a normal diet, but have been modified to physiological roles beyond the provision of simple nutrient. Similarly, the compositions described herein may be presented in dosage forms such as in a capsule. Again, amounts of the active isolated molecule will vary depending on the particular food or beverage and may contain any amount up to about 100% of the product, especially when formulated as an ingestible capsule. It is also understood by one of skill in the art that the molecules described herein, whether isolated or provided as within a culture fraction, can be combined with the use of probiotic bacteria in methods of treatment or for nutritional supplementation.

EXAMPLES

Summary

Figure 1:
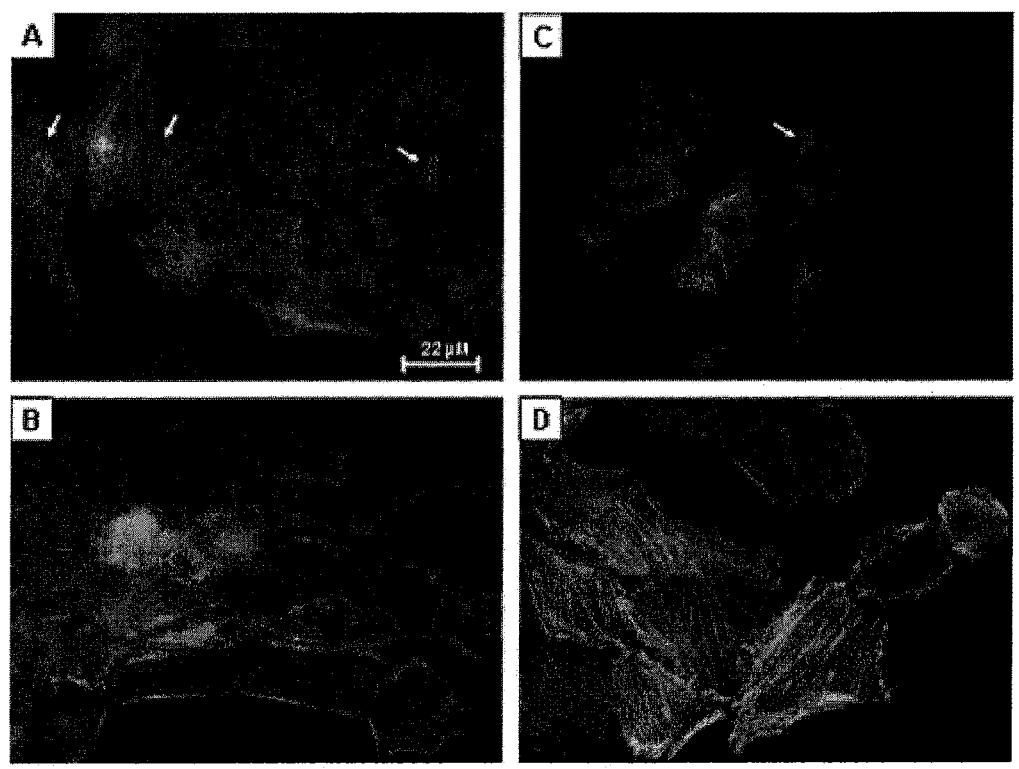
FIG. 1. Fluorescent micrographs of HEp-2 cells incubated for 6 h with EHEC strain 43984. Bright fluorescence with the fluorescein isothiocyanate-phalloidin stain, indicating aggregation of foci of alpha-actinin underneath adherent EHEC (arrows) was visualized under the microcolonies by fluorescence microscopy. (A) Infected cells; (B) Non-infected cells; (C) EHEC infected cells co-incubated with 40 µl of peptide fraction of *L. acidophilus* La5; and (D) EHEC LuxS (-ve) infected cells. Original magnification, 40×. Bar, 22 µm. Images are representative of three independent assays.

*Lactobacillus acidophilus* La-5 CFSM Decreased *E. coli* O157:H7 Attachment to Tissue Culture Cells It was previously demonstrated that *L. acidophilus* La-5 SM influenced EHEC O157 T3SS (29). Down-regulation of important virulence-related gene expression was presently detected after EHEC O157 was grown in medium supplemented with biologically active fractions of *L. acidophilus* La-5 CFSM (La-5 fractions) when compared with EHEC O157 grown in the same medium without the addition of La-5 fractions. Presently it was demonstrated that the addition of La-5 fraction would have an influence on EHEC O157 adhesion to eukaryotic cells in vitro and in vivo. Adhesion and AE lesion formation in eukaryotic cells (HEp-2 and HeLa cell lines, respectively) were substantially reduced when La-5 fractions were added before exposure to *E. coli* O157:H7 strain ATCC 43894. Infection of HeLa cells with EHEC O157 alone showed typical localized adherence behavior (FIG. 1A). However, when it was coincubated with La-5 fraction we could visualize the reduction of actin accumulation underneath attached bacteria (FIG. 1C). HeLa cells infected with EHEC O157 LuxS$^-$ in the presence of propanolol showed no evidence of actin accumulation (FIG. 1D); comparable to non-infected HeLa cells incubated only with the La-5 CFSM selected fraction (F34) (FIG. 1B). To complement the FAS test we performed the adhesion assay with the same EHEC O157 strain 43894 on the HEp-2 cell line. The results of the adhesion assay are summarized in Table 1. Infection of HEp-2 cells with EHEC O157 was normalized to 100% in order to compare with the La-5 treated cells. The degree of attachment was reduced by 76% in the wells containing the La-5 biologically active fraction.

TABLE 1

Adherence of EHEC O157 strains to HEp-2 cells.

| Bacteria | % Adherence$^b$ |
|---|---|
| EHEC 43894 | 100$^{a*}$ |
| EHEC 43894 coincubated with 10% *L. acidophilus* La5 fraction 33 | 26* |
| EHEC 43894 coincubated with 10% *L. acidophilus* La5 fraction 34 | 24* |
| EHEC VS94 luxS (−)ve + β-blocker | 22 |
| EHEC VS94 luxS (−)ve no β-blocker | 64 |

$^a$EHEC 43894 control group CPU ml$^{-1}$ were normalized to 100% adherence ability.
$^b$The results are average values of three independent replicates.
*Statistically significant value (P = 0.001 [student t test]).

Adherence of EHEC to human epithelial cells involves the activation of the adhesin intimin, an outer membrane protein encoded by the eae gene (9, 26, 27, 37). Previous work (27) showed that production of intimin-specific antisera blocked adherence of EHEC to HEp-2 cells. The immunogenic capacity of intimin has been extensively studied in order to develop anti-EHEC and anti-EPEC vaccines (6, 7, 12, 28). The results demonstrate that secreted molecules from probiotic bacteria could be used to prevent EHEC adherence to epithelial cells in tissue culture models. Relationship Between Infectious Dose of EHEC and Bioluminescent Imaging in ICR Mice.

The optimal infectious dose of EHEC for the bioluminescent imaging of bacterial colonization on SPF ICR mice was determined. Five different cell concentrations, ranging from $10^5$ to $10^9$ cells per dose, were used for a single challenge with EHEC O157 bioluminescent strain. The bioluminescent signal for mice infected with $10^5$ cells was very weak throughout the experiment and only at an inoculation of $10^7$ CFU or greater was the signal strong enough to be visualized and computed (Table 2). Based on previous work in which EHEC O157 proliferated in mice intestines within 24 h of infection (2), it was expected that a dose of $10^5$ CFU would have been enough to emit a strong light output. The aim was to monitor EHEC O157 colonization in vivo in a short period of time, an inoculation dose of $10^8$ CFU was selected for the challenge studies.

TABLE 2

Areas of maximum bioluminescence in EHEC O157 infected mice calculated in terms of relative light unit counts per $cm^2$ per sec.

| Mice experimental group | Mean Grey (cts $[cm^2\ s^{-1}]^{-1})^{a,b}$ |
|---|---|
| EHEC $3^{rd}$ day (control group) | $4002 \pm 544^{ns}$ |
| EHEC-probiotic 3rd day | $5171 \pm 637^{ns}$ |
| Probiotic-EHEC 3rd day | $4065 \pm 884^{ns}$ |
| EHEC $5^{th}$ day (control group) | $21965 \pm 4871^*$ |
| EHEC-probiotic 5th day | $2176 \pm 635^*$ |
| Probiotic-EHEC 5th day | $792 \pm 82^*$ |
| EHEC $7^{th}$ day (control group) | $NA^c$ |
| EHEC-Probiotic 7th day | $875 \pm 172^c$ |
| Probiotic-EHEC 7th day | $422 \pm 1493^c$ |
| Dose-response assay | |
| EHEC $10^5\ 3^{rd}$ day | $1900 \pm 178$ |
| EHEC $10^6\ 3^{rd}$ day | $2683.8 \pm 65$ |
| EHEC $10^7\ 3^{rd}$ day | $3364.85 \pm 450$ |
| EHEC $10^8\ 3^{rd}$ day | $5262.8 \pm 391$ |
| EHEC $10^9\ 3^{rd}$ day | $27998 \pm 3059$ |

$^a$Areas of maximum bioluminescence were calculated in terms of relative light unit counts per $cm^2$ per sec (cts $[cm^2\ s^{-1}]^{-1}$)
$^b$The results are means ± standard deviations of three replicates.
$^c$Control group did not survive to this point
*Statistically significant value (P < 0.05 [student t test])
$^{ns}$Not statistically significant value (P > 0.05 [student t test])

*L. acidophilus* La-5 Biologically Active Fraction Reduces Attachment of EHEC to Intestinal Epithelium of ICR Mice.

Figure 3:
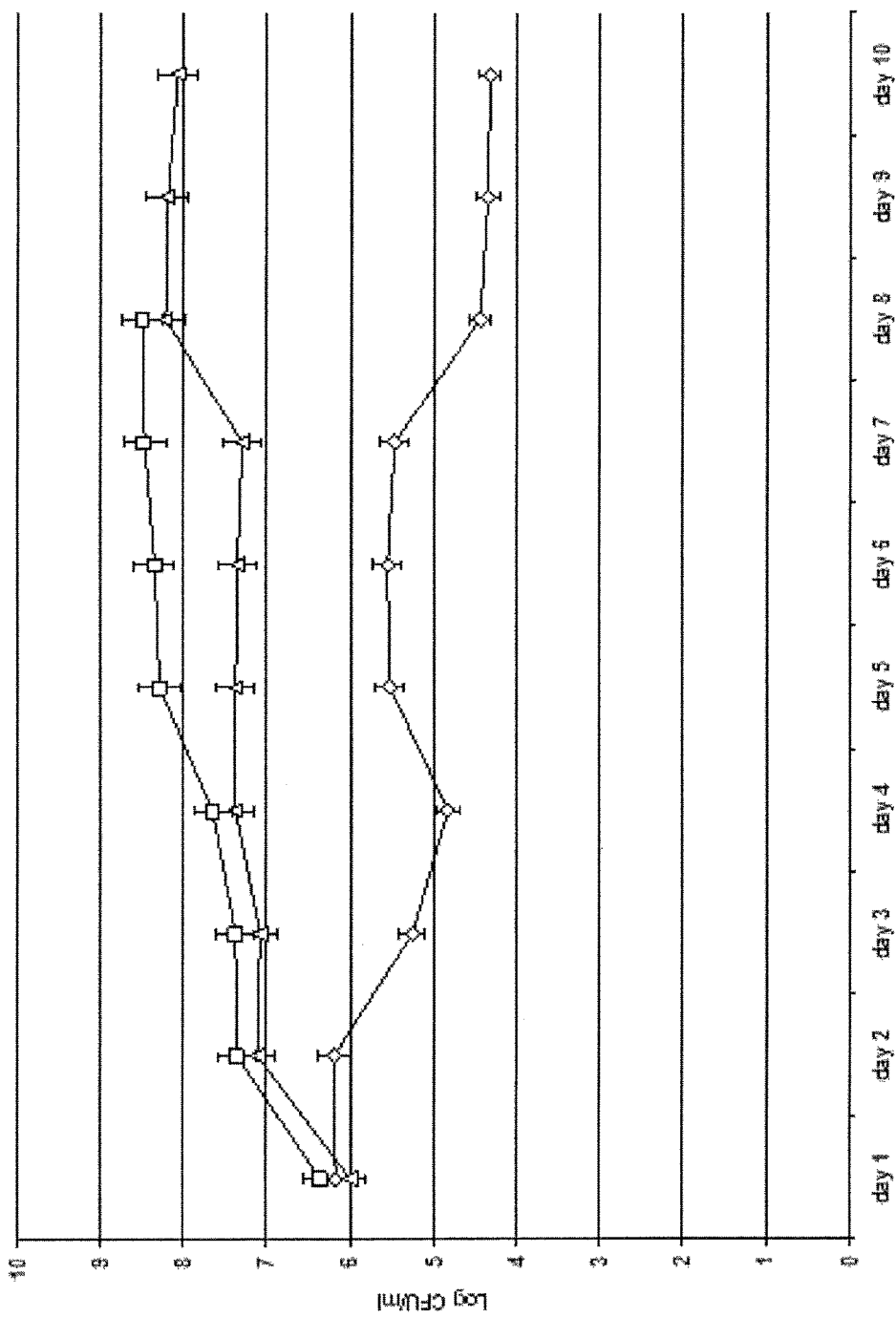
FIG. 3. Average daily fecal shedding of EHEC O157. (◊) group 2 (probiotic-EHEC), (Δ) group 3 (EHEC-probiotic) and (□) group 4 (positive control). The data are average daily fecal values of each group (means±standard deviations, n=5).
Figure 4:
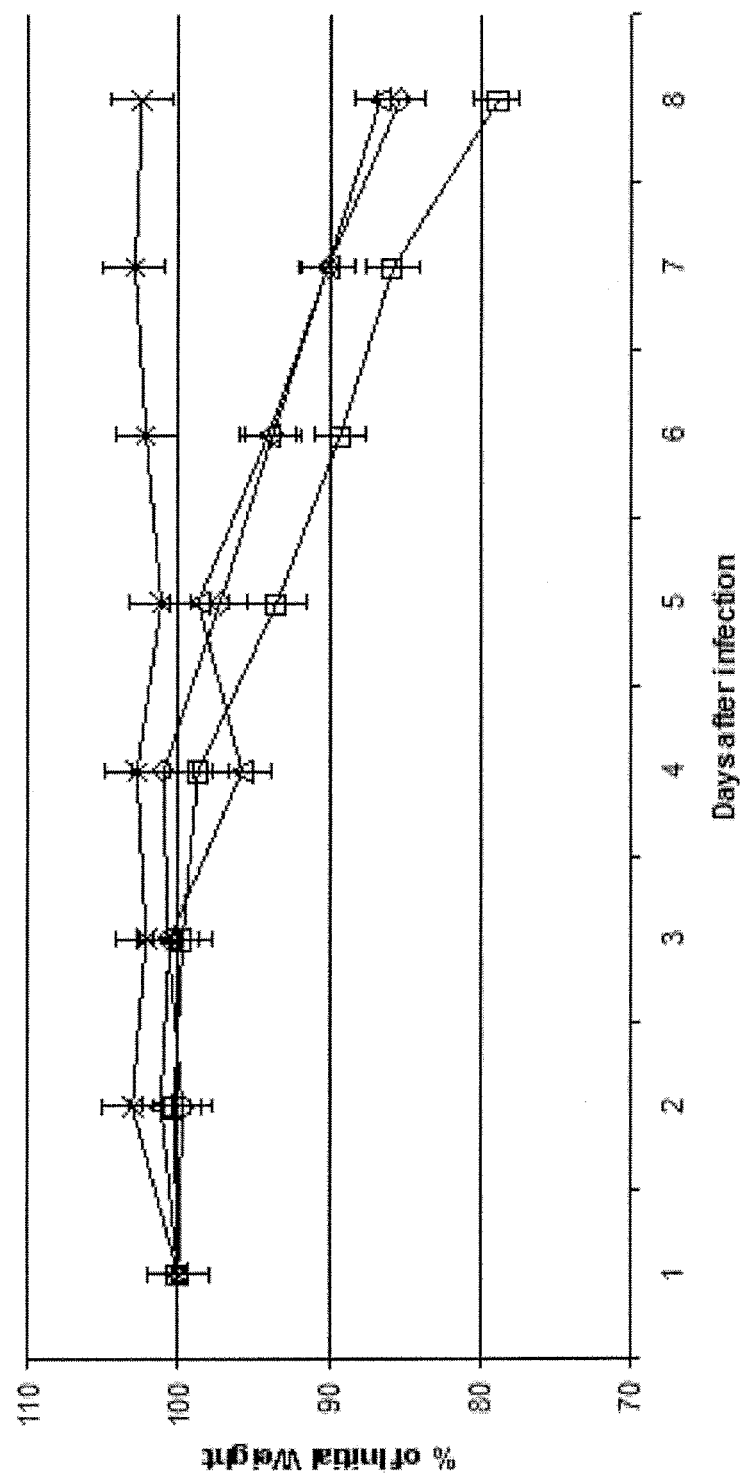
FIG. 4. Body weights of mice during the week following challenge indicated as percentage of initial weights. (x) group 1 (negative control), (◊) group 2 (probiotic-EHEC), (Δ) group 3 (EHEC-probiotic) and (□) group 4 (positive control). The data are average daily weight values of each group (means±standard deviations, n=5).

The ability of EHEC O157 to colonize mice treated with the probiotic La-5 fraction and non-treated ICR mice was compared. EHEC O157 was recovered from the feces of all groups of mice that were infected with the organism (i.e. groups 2, 3 and 4) throughout the study. The proportion of mice shedding EHEC O157 declined significantly over the course of the study in animals that received the La-5 fraction (groups 2 and 3; P=0.0004 and P=0.002, respectively); however, the fecal shedding in mice that were infected with EHEC O157 in the absence of the fraction (group 4) increased to $10^9$ CFU $g^{-1}$ after the fifth day post-infection (FIG. 3). At this time mice from group 4 were showing signs of dehydration and physical deterioration and were re-evaluated every 8 h (FIG. 4). Three mice from group 4 died within the evaluation period and the rest showed a significant reduction in body temperature (<34° C.). At day 5, the end point of group 4 was reached and the remaining mice were euthanized (Table 3). For groups 2 and 3, the condition of the mice remained acceptable ten days post-infection.

TABLE 3

Mice average body conditioning scoring and survival rate 7 days after challenge with EHEC O157:H7.

| Mice experimental group | Body temperature (° C.)$^a$ | Rough hair coat (+/−)$^{*b}$ | Lethargic (+/−)$^{*b}$ | Survival rate by $5^{th}$ day $^b$ |
|---|---|---|---|---|
| Group 1 (negative control) | 38.2 ± 0.17 | − | − | 5/5 |
| Group 2 (probiotic-EHEC) | 33.3 ± 1.7 | + | − | 5/5 |
| Group 3 (EHEC-probiotic) | 33.6 ± 1.3 | ++ | − | 5/5 |
| Group 4 (positive control) | 30.9 ± 1.3 | +++ | +++ | 2/5 |

Figure 2:
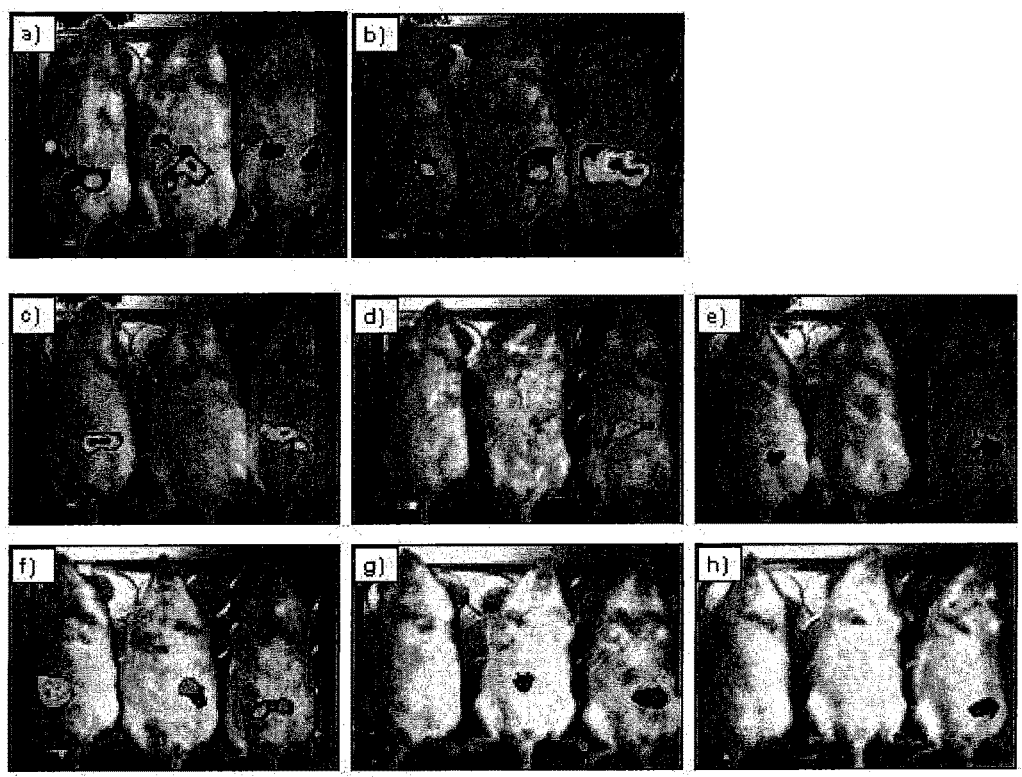
FIG. 2. Bioluminescence images from $10^8$ CFU EHEC O157 infected mice. Images were obtained on the $3^{rd}$, $5^{th}$, and $7^{th}$ day post-infection. Areas in which luminescent EHEC O157 is present are shown as color-overlay.

$^a$Data are means ± standard deviations of three group (n = 5) replicates
$^b$Signs of deterioration and survival rate are averages of three group (n = 5) replicates
*(+) represents the presence of the sign of deterioration, (−) represents the absence of the sign of deterioration Bioluminescent signals from mice in groups 2, 3 and 4 were taken and analyzed in order to compare their light intensities at the specified times. On the third day of the experiment, all mice were orally infected with $10^8$ CFU EHEC O157. Bioluminescence was monitored on the third, fifth and seventh day after infection. On the third day after infection, strong bioluminescence was observed in the gastrointestinal (GI) tract of all mice in groups 4 (FIG. 2a) and 3 (FIG. 2c), and two mice from group 2 (FIG. 2f). There was no significant difference in bioluminescence values from all groups of mice at the third day post-infection. However, significant differences were observed after the fifth day post-infection as one mouse from group 2 (FIG. 2g) and two mice from group 3 (FIG. 2d) showed no bioluminescent signal. However, the mouse producing the positive signal from group 3 (FIG. 2d) exhibited strong bioluminescence when compared to the weak bioluminescent signal emanating from the two mice in group 2 (FIG. 2g). Bioluminescence observed at the seventh day post-infection was greatly decreased in both probiotic treated groups indicating that the probiotic La-5 fraction is capable of inhibiting EHEC O157 attachment to intestinal epithelial cells (FIG. 2e and FIG. 2h). It has been proposed that the presence of probiotic bacteria in the host gastrointestinal tract enhances immunity; thereby protecting the host against bacterial infections (11, 13, 31, 32). Taking into account the strain specificity of probiotics (2), employed cell-free spent medium was selected and employed from a probiotic bacterium that down-regulated virulence related genes of EHEC in vitro (29). Due to the ability of probiotic cells to protect animal and human hosts once present in their GI tract (14-16, 30, 33, 38), certain experiments described herein focused on the role of probiotic secreted molecules in the control of infection.

Activity Against Other Enteric Pathogens

The effects of secreted molecules of *L. acidophilus* LA-5 and several strains of *Bifidobacteria* against *Salmonella enterica* serovar *Typhimurium* virulence gene expression were also demonstrated. The selection of hilA (Hyper Invasive Locus) gene for the gene fusion assay was based on its importance on the gene transcription of the type III secretion system (TTSS) encoded within *Salmonella* pathogenicity island 1 (SPI1). The bacterial strains and constructs used in this part of the study are shown in Table 4.

TABLE 4

Bacterial strains and constructs used to
study effects on hila (luxCDABE::hilA)

| Strain, plasmid, or construct | Serotype | Relevant genotype/property | Reference |
|---|---|---|---|
| Strains | | | |
| L. acidophilus LA-5 | | Probiotic lactic acid bacteria | CRIFS stock[a] |
| B. longum | | Probiotic lactic acid bacteria | CRIFS stock[a] |
| B. bifidum | | Probiotic lactic acid bacteria | CRIFS stock[a] |
| B. infantis | | Probiotic lactic acid bacteria | CRIFS stock[a] |
| B. crudilactis | | Probiotic lactic acid bacteria | (Delcenserie et al., 2008) |
| Constructs E. coli | | | |
| ATCC 43888 (C1) | O157:H7 | Stx-, LEE1::lux | (Medellin-Pena et al., 2007) |

[a]CRIFS stock strains are deposited in the Canadian Research Institute for Food Safety (CRIFS) culture collection.

Figure 5:
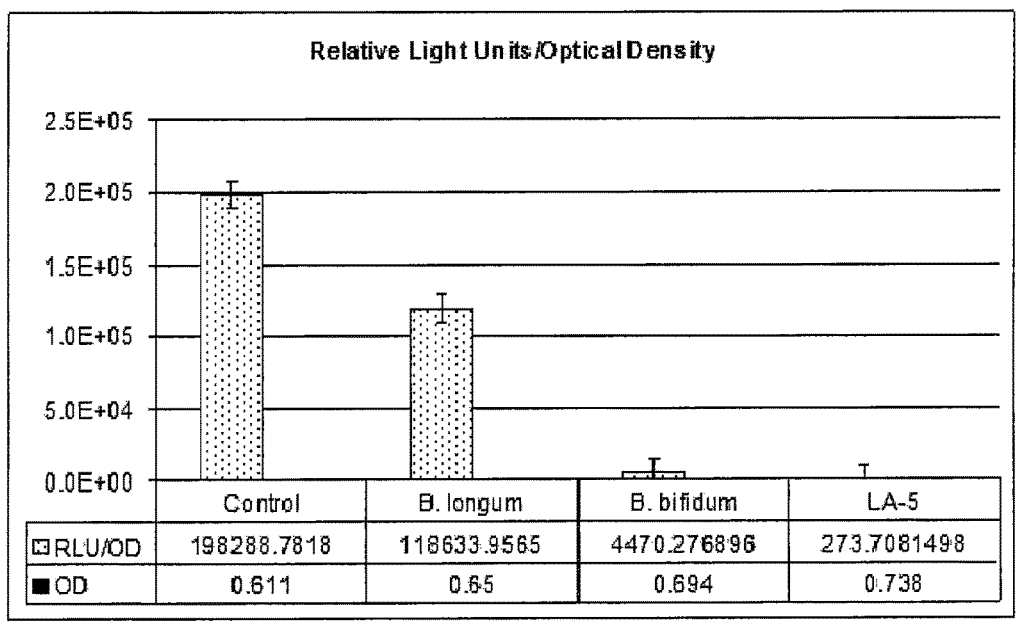
FIG. 5. Effect of LA-5 cell-free spent medium fraction (F54) and *Bifidobacteria* CFSM on the induction of hilA in *Salmonella Typhimurium* via LuxS assay. Standard deviations from the mean are calculated from 2 independent trials with 3 wells per trial. Expression of hilA gene is monitored by luminescence (RLU) produced by the *Salmonella* construct.

Probiotics cell-free spent medium (CFSM) and CFSM fractionated by size exclusion chromatography (SEC) were studied by the LuxS gene fusion assay. LuxS assay was used to determine the expression of hilA (luxCDABE::hilA). Neither Bifidobacteria CFSM nor LA-5 CFSM fraction (F54) affected the growth rates of Salmonella (FIG. 5). When determined by the LuxS assay, CFSM were found to have an inhibitory effect on the hilA expression compared to the control (FIG. 5).

Activity Produced by Other Probiotic Bacteria

Figure 6:
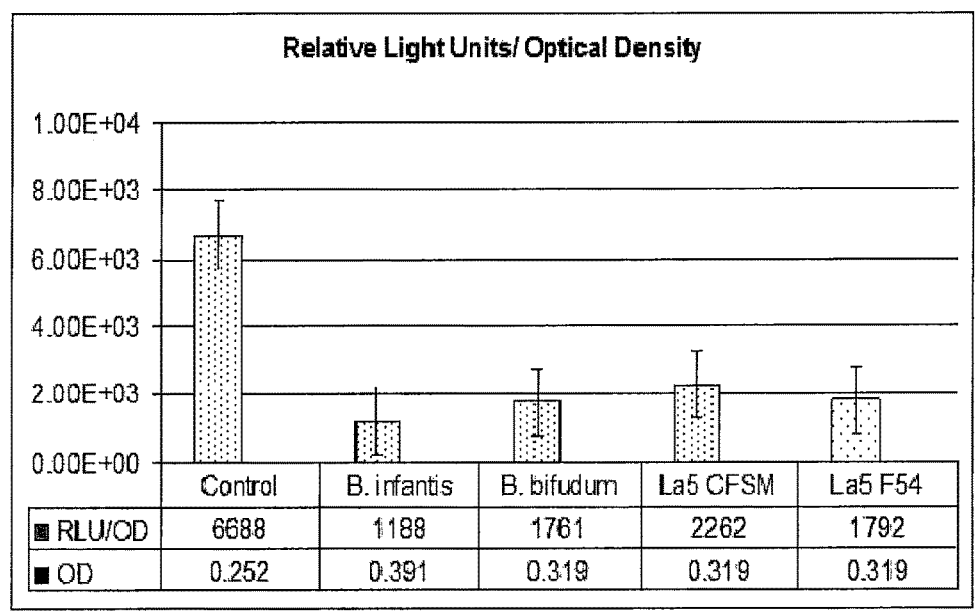
FIG. 6. Effect of LA-5 and *Bifidobacteria* CFSM and CFSM fractions (F54) on the induction of LEE1 in Enterohaemorrhagic *E. coli* O157:H7 via LuxS assay. Standard deviations from the mean are calculated from 2 independent trials with 3 wells per trial. Expression of LEE1 is monitored by luminescence (RLU) produced by the *E. coli* O157:H7 construct.

The effects of secreted molecules of several strains of proven probiotic bacteria were also tested: Bifidobacterium longum, Bifidobacterium bifidum, Bifidobacterium infantis, Bifidobacterium crudilactis and three Bifidobacterial species not yet named against enterohaemorrhagic Escherichia coli O157:H7 and Salmonella enterica serovar Typhimurium virulence gene expression via the LuxS assay. Results from these experiments showed that the probiotic strains contain molecules that work in a L. acidophilus LA-5-like manner inhibiting induction of LEE1 in enterohaemorrhagic E. coli O157:H7 (FIG. 6) and hilA in S. Typhimurium (FIG. 5). Neither Bifidobacteria CFSM nor LA-5 CFSM fraction (F54) affected the growth rates of Salmonella (FIG. 5) and enterohaemorrhagic E. coli O157:H7 (FIG. 6). These preliminary results show differences in inhibitory activity but it is believed due to molecule(s) concentration. All probiotic strains grow at different rates and the protocol used for collecting the bacterial cell-free spent medium was following a 24 h period, since the growth period according to growth rate differences was standardized.

The effect of medium conditioned by the growth of probiotic strains on the expression of virulence-associated genes in E. coli O157:H7 was further characterized as follows to identify further stains of probiotic bacteria effective against EHEC: (1) The activation or repression of LEE operons was monitored using EHEC strain (ATCC 43894) transformed with gene reporter constructs containing luciferase gene luxCDABE (kindly provided by Dr. Haifeng Wang). These constructs operate under the transcriptional control of the LEE promoters. The expression of LEE operons was measured as light emission produced by E. coli O157:H7 constructs after exposure to medium conditioned by the growth of the probiotic strains. Probiotic strains used and found effective: Lactobacillus reuteri (RC14) (control), Lactobacillus fermentum (LFER), Lactobacillus rhamnosus (GR1), Lactococcus lactis (LL), Lactobacillus acidophilus La5 (LA5) and Streptoccocus thermophilus (STTH).

Identification of the Active Secreted Molecules

Extracellular fractions from B. infantis cultures were studied after 24 h growth. After centrifugation (6000 g, 10 min) of 1 liter of culture, the supernatant was filtered through cellulose acetate membrane filters (pore size: 0.22 µm). The cell-free spent medium (CFSM) was then concentrated via lyophilisation to 1/100 of the original volume. The lyophilized CFSM was resuspended in molecular Biology grade water and separated by size exclusion chromatography (SEC) and the active fractions were stored at −20° C. for further analysis. Ion exchange chromatography (IEC) was used following the SEC since this is suitable for sample fractionation, purification and screening. The different fractions (basic and acidic proteins concentrated by IEC and their flow-troughs) were then analyzed with the LuxS assay to determine which one of these fractions possesses the desired activity. After we confirm the presence of active molecules the fractions will be used in multidimensional analysis, such as 2-D gel electrophoresis and HPLC. At the same time we will carry out tissue culture assays with Salmonella enterica serovar Typhimurium and possibly other foodborne pathogens.

Figure 7:
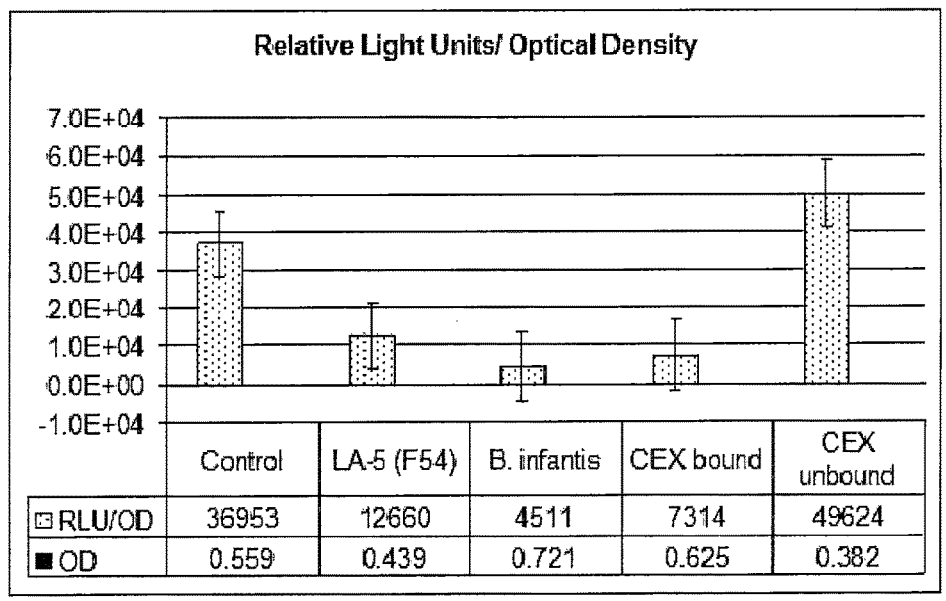
FIG. 7. Effect of LA-5 and *Bifidobacteria* CFSM (CFSM fraction 54 [F54] separated by cation exchange chromatography [CEX]) on the induction of LEE1 in Enterohaemorrhagic *E. coli* O157:H7 via LuxS assay. Standard deviations from the mean are calculated from 2 independent trials with 3 wells per trial. Expression of LEE1 is monitored by luminescence (RLU) produced by the *E. coli* O157:H7 construct.
Figure 8:
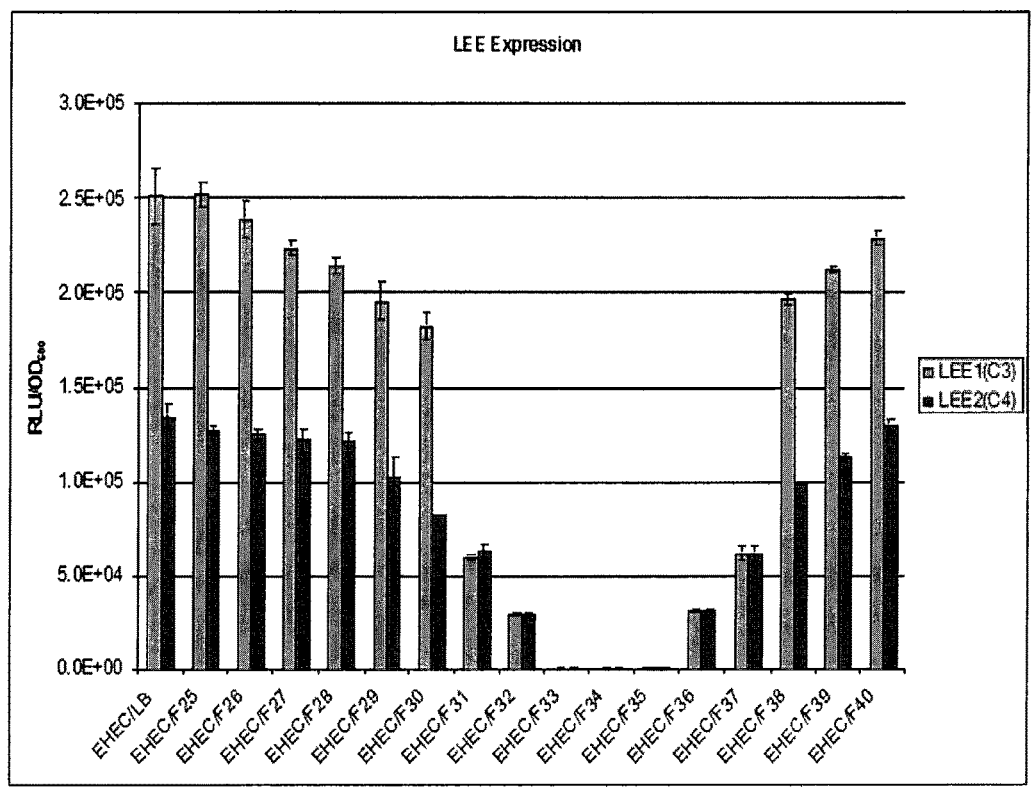
FIG. 8. Luminescence activity of LEE1::luxCDABE and LEE2::luxCDABE fusions in *E. coli* O157:H7 (C3, C4) grown in LB broth alone (EHEC/LB) or in LB broth supplemented with 10% of *L. acidophilus* La-5 CFSM fractions 25 to 40 (EHEC/F). Data was collected after 16 h growth. Results were expressed as relative light units (RLU) defined as counts min$^{-1}$ and adjusted to $OD_{600}$ (RLU/$OD_{600}$). The data are mean±SD values of three independent replicates.
Figure 9:
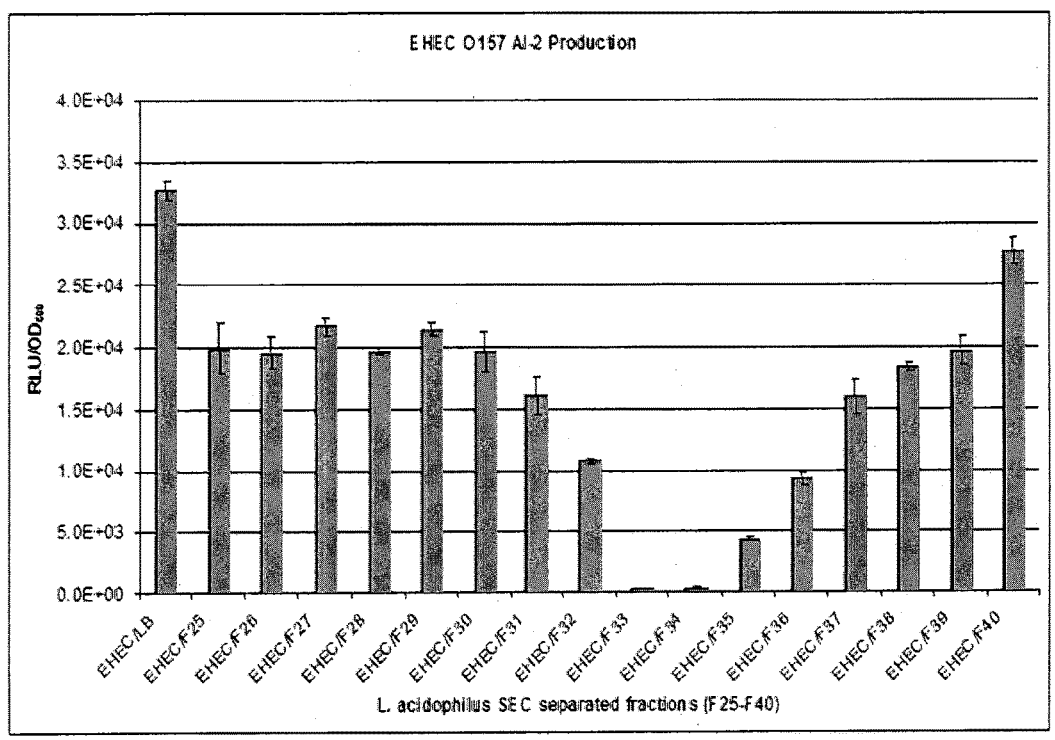
FIG. 9. Autoinducer-2 bioassay conducted three times with the same samples. EHEC O157:H7 (ATCC 43894) was grown for 16 h in LB broth alone (EHEC/LB) or supplemented with 10% of *L. acidophilus* La-5 CFSM fractions 25 to 40 (EHEC/F). The cell-free supernatants from these cultures were collected as described in the methods section. Results were expressed as relative light units (RLU) defined as counts min$^{-1}$ and adjusted to $OD_{600}$ (RLU/$OD_{600}$). The data are mean±SD values of three independent replicates.

Preliminary results show that B. infantis CFSM active molecule bound to the cation exchange chromatography column (Aurum CEX, BioRad) suggesting that the molecules may be a small signal peptide possessing basic amino acids residues (FIG. 7).

The first step of separation of molecules from bulk quantities was performed by using size exclusion chromatography (SEC). Following the separated fractions, EHEC O157:H7 bioassays were performed to confirm the presence of the biologically active molecule(s). Consequently, analysis of the biologically active fractions was carried out by electrospray mass spectroscopy (ES-MS) and nuclear magnetic resonance (NMR). Results from the ES-MS and NMR showed that the biologically active fractions were still excessively complex, evading a conclusive report of the nature of the studied fractions. Biologically active fractions were subjected to pH sensitivity, enzymatic and temperature treatments in order to try to shed some light in their nature. Results from these tests, indicated that the biologically active fractions could be very small and of protein nature. Pursuing the necessity for purification, the biologically active fractions were further separated by low-pressure SEC and fractions collected were read at 214 and 280 nm wavelengths and tested again for activity against EHEC O157:H7. Four peaks were collected from which two were still active in vitro. The biologically active fractions consisted of four peptide peaks that were sent for peptide sequencing and the sequences provided herein in the example section.

Effects of the Secreted Molecules on Viruses

MNV-1 viral load was measured in RAW 264.7 cells with and without treatment with probiotic CFSM. It was found that the probiotic CFSM reduced viral load in these cells, thereby implying that MNV-1 propagation is negatively affected by the presence of probiotic molecules in the CFSM.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Examples

Example 1

Cell-Free Fractions

Cell-free fractions were prepared as previously described (25). Briefly, *Lactobacillus acidophilus* strain La-5 was grown overnight in modified DeMann, Rogosa and Sharpe medium. (mMRS; 10 g peptone from casein, 8 g meat extract, 4 g yeast extract, 8 g D(+)-glucose, 2 g dipotassium hydrogen phosphate, 2 g di-ammonium hydrogen citrate, 5 g sodium acetate, 0.2 g magnesium sulfate, 0.04 g manganese sulfate in 1 L distilled water) (MRS; BD Diagnostic Systems, Sparks, Md.). The overnight culture was diluted 1:100 in fresh medium. When the culture grew to an optical density at 600 nm ($OD_{600}$) of 1.6 ($1.2 \times 10^8$ cells/ml), the cells were harvested by centrifugation at 6,000×g for 10 min at 4° C. The supernatant was sterilized by filtering through a 0.2-µm-pore-size filter (Millipore, Bioscience Division, Mississauga, ON, Canada) and will be referred to as cell-free spent medium (CFSM). Two liters of *L. acidophilus* La-5 CFSM was collected and freeze-dried (Unitop 600 SL, VirTis Co., Inc. Gardiner, N.Y., USA). The freeze-dried CFSM was reconstituted with 200 ml of 18-Ω water. The total protein content of the reconstituted CFSM was quantified using the BioRad DC protein assay kit II (Bio-Rad Laboratories Ltd., Mississauga, ON, Canada). Freeze-dried CFSM was stored at −20° C. prior to the assays.

Example 2

Fractionation of the *L. acidophilus* La-5 CFSM

Five millilitres of CFSM were directly deposited on a P2 Biogel (Bio-Rad, Missasauga, ON., Canada) column (exclusion, 100 to 1,800 Da; 2.5×100 cm; Bio-Rad Laboratories Ltd.) and run at room temperature in 18-Ω water at a gravity flow rate of 0.8 ml/min, and eighty 5 ml fractions were collected. The fractions collected were freeze-dried and resuspended in 1 ml 18-Ω water for preliminary screening against EHEC LEE1, LEE2 and AI-2 production as previously described (29). The total protein content of the fractions was quantified using the BioRad DC protein assay kit II. Fractions showing a strong inhibitory activity against LEE expression and AI-2 production were selected.

Example 3

Bacterial Strains

The bacterial strains used in this study are described in Table 5. *L. acidophilus* strain La-5 was grown under anaerobic conditions at 37° C. in mMRS medium (29). *E. coli* O157:H7 strain VS94 (36) was grown in Luria-Bertani broth (LB) (BD Diagnostic Systems). The bioluminescent strain of *E. coli* O157:H7 (luxCDABE) was grown in LB agar supplemented with ampicillin (Amp) and kanamycin (Km) (Sigma-Aldrich Canada Ltd., Oakville, ON, Canada) at a concentration each of 50 µg/ml and incubated overnight at 37° C. A single colony was taken from the plate and subcultured in LB broth and high glucose Dulbecco's minimum essential medium (DMEM/High) (Sigma-Aldrich Canada Ltd.) supplemented with the antibiotics and incubated overnight at 37° C. on a shaker at 150 rpm. The correlation between luminescence and cell count in LB broth was established by a standard plate count technique and by the measurement of the bioluminescence for 1 ml of culture serial dilutions with a tube luminometer (MGM Instruments, Hamden, Conn.). For the infection of the mice, an overnight culture was centrifuged at 13,000×g for 10 min, washed, and resuspended in fresh antibiotic supplemented LB broth.

TABLE 5

Bacterial strains and constructs used in this study

| Strain, plasmid, or construct | Serotype | Relevant genotype/property | Reference |
|---|---|---|---|
| Strains | | | |
| *E. coli* | | | |
| VS94 | O157:H7 | luxS negative | 21 |
| ATCC 43894 | O157:H7 | Stx1+ and Stx2+, isolated from human stool. Michigan, USA | CRIFS stock[a] |
| *L. acidophilus* La-5 | | Probiotic lactic acid bacteria | CRIFS stock[a] |
| Constructs | | | |
| *E. coli* | | | |
| ATCC 43894 (C4) | O157:H7 | Stx1+ and Stx2+, LEE2::lux | 15 |

[a]CRIFS stock strains are deposited in the Canadian Research Institute for Food Safety (CRIFS) culture collection.

Example 4

Fluorescent Staining of Actin Filaments

The FAS tests were performed as described previously (23) with some modifications. HeLa, human cervix adenocarcinoma epithelial cells, were provided by Dr. Roger Johnson (Laboratory for Foodborne Zoonoses, Public Health Agency of Canada). HeLa cells were grown in complete Eagle's minimal essential medium (EMEM) (Sigma-Aldrich Canada Ltd.) supplemented with 2% (v/v) fetal bovine serum (FBS) (Invitrogen Canada Inc., Burlington, ON, Canada). Cells were then plated onto 4-well micro-chamber slides at $2 \times 10^5$ cells $ml^{-1}$ and incubated for 24 h in the presence of 5% $CO_2$. The cells were then maintained during the assay in serum and antibiotic free EMEM. Before inoculation with bacteria, selected fractions of *L. acidophilus* CFSM (F33 and F34) were added to treatment group wells. As a negative control for AE lesion formation we used an *E. coli* O157:H7 luxS-negative strain. The negative control group wells were inoculated with $10^5$ *E. coli* O157:H7 strain VS94 with or without supplementation with 100 µM propanolol, and with only the selected fractions of *L. acidophilus*. Propanolol was used to suppress complementation of the AE phenotype by the hormones epinephrine and norepinephrine produced by the eukaryotic cells. After inoculation of EHEC O157 strain 43894 into treatment and positive control wells, the slides were incubated for 6 h at 37° C. in the presence of 5% $CO_2$. The cells were then washed three times with phosphate-buffered saline (PBS) and fresh medium was added. Cells were incubated for another 3 h and then washed six times with PBS and fixed in 4% paraformaldehyde. Fixed and washed cells were permeabilized by treating slides with 0.1% Triton X-100 in PBS for 15 min. Cells were incubated with 0.2% bovine serum albumin (BSA) (Invitrogen Canada Inc.) in PBS for 1 h. After three washes in PBS, slides were treated with a 10 µg/ml solution of fluorescein isothiocyanate (FITC) conjugated phalloidin (Sigma-Aldrich Canada Ltd.) in PBS for 40 min to specifically stain actin filaments. Slides were washed three times in PBS and then examined with a Zeiss Axioskope 2 microscope with fluorescence filters for FITC (Carl Zeiss Canada, Inc., North York, ON, Canada). Images were recorded using the Axiocam and Zeiss Axiovision Software (Carl Zeiss Canada, Inc.).

Example 5

HEp-2 Cell Adhesion Assay

In order to compare levels of adherence to HEp-2 epithelial cells in culture, we used an established model for evaluating adherence of EHEC O157:H7 (27). HEp-2, human laryngeal carcinoma epithelial cells, were a kind gift from Dr. Carlton Gyles (Department of Pathobiology, University of Guelph). Briefly, HEp-2 cells grown in EMEM supplemented with 10% (v/v) FBS were plated onto 24-well tissue culture plates at $2 \times 10^5$ cells ml$^{-1}$ and incubated for 24 h in the presence of 5% $CO_2$. The cells were then maintained during the assay in serum and antibiotic-free EMEM. Before inoculation with bacteria, 10% (v/v) of *L. acidophilus* CFSM selected fractions were added in triplicate to treatment group wells. Wells containing the negative control groups were inoculated with $10^5$ *E. coli* O157:H7 strain VS94 with or without supplementation with 100 µM propanolol (Sigma-Aldrich Canada Ltd.). Following inoculation of $10^5$ EHEC O157 into treatment and control group wells, the plates were incubated for 3 h at 37° C. in the presence of 5% $CO_2$. The cell monolayers were then washed three times with PBS to remove non-adhering bacteria and fresh medium was added. Cells were incubated for another 3 h and then washed six times with PBS. Washed cells were lysed with 0.1% Triton X-100. Released bacteria present in the suspension were collected and appropriate dilutions were plated on LB agar. To evaluate if the percentage of adherence in the treatment groups was significantly different from that of the control group, where the recovered counts from the control group ($2.2 \times 10^7$ CFU ml$^{-1}$) were considered to be 100%, the percentage of adherence in the negative control and treatment groups were calculated using the following equation.

$$\% \text{ of Recovery} = \frac{\text{Group } CFU \text{ ml}^{-1} \times 100}{2.2 \times 10^7}$$

Example 6

Mice Colonization Experiments

SPF female ICR mice were obtained at 3 weeks of age from Taconic Farms (Hudson, N.Y.), and used for the experiments after one-week acclimation. Mice were housed at the Isolation Unit of the Central Animal Facility (University of Guelph) in a temperature controlled environment with a 12 h light/dark cycle. Animal care was provided in accordance with the animal utilization protocol no. 04R030 (University of Guelph) and the *Guide to the Care and Use of Experimental Animals* (1). Mice were fed sterilized solid rodent chow and water. When needed, water was supplemented with Amp and Km at a concentration of 400 mg L$^{-1}$ and 200 mg L$^{-1}$, respectively. Each mouse was assessed daily for weight, body temperature, signs of dehydration, posture and alertness.

Example 7

Mice Experiments

Dose-Response Experiments

Ten mice were divided into 5 equal groups (n=2), and each group was infected by oral gavage with 100 µl of bacterial cell suspension containing $10^5$ to $10^9$ cells. Mice were given the antibiotics required for selection of the luxCDABE-encoding plasmid in their drinking water at concentrations mentioned previously. Sucrose (5% w/v) (Sigma-Aldrich Canada Ltd.) was added in order to make the water supplemented with the antibiotics palatable. The 5% sucrose solution supplemented with the antibiotics was changed daily.

Feeding-Infection Experiments

Mice were divided into four groups. Group 1 was fed with 100 µl of La-5 fraction (negative control) (n=5); groups 2 and 3 were fed daily with 100 µl of La-5 fraction 2 days before (probiotic-EHEC) and 2 days after (EHEC-probiotic) challenge with $10^8$ CFU ml$^{-1}$ EHEC, respectively (n=5); and group 4 (positive control) was infected with $10^8$ CFU ml$^{-1}$ EHEC (n=5). Feeding-infection experiments were repeated three times.

Bioluminescent Imaging

Bioluminescent imaging was performed as previously described (4) with minor modifications. Briefly, bioluminescent imaging was monitored on the $3^{rd}$, $5^{th}$ and $7^{th}$ day after infection. Prior to imaging, mice were anesthetized with a cocktail composed of ketamine (60 mg kg$^{-1}$) and medetomidine (0.75 mg kg$^{-1}$). Atipamezole (2.25 mg kg$^{-1}$) was used to reverse the effects of the anesthetics. All drugs were administered intraperitoneally. Both bioluminescent and photo images of mice were taken with a cooled slow-scan CCD camera (NightOWL Molecular Imager, EG&G Berthold Technologies, Wildbad, Germany). The integration time for bioluminescence was one minute at low resolution. Images were processed with the WinLight software (EG&G Berthold). Pseudocolor images were obtained to represent the distribution of bioluminescent intensity, which changed from blue to yellow to red with increasing light output. Bioluminescent images were superimposed onto photo images of the same mice to locate the origin of bioluminescence. The areas of maximum bioluminescence were identified with the use of the 2D peak search option of the software, and light output from these areas was calculated in terms of relative light unit counts per cm$^2$ per sec (cts [cm$^2$ s$^{-1}$]$^{-1}$) with the WinLight program. The dose-response experiment was carried out over 7 days. The feeding-infection experiment was carried out over 12 days or until the end point of the experiment (indicated by a body temperature of <34° C. and/or loss of 20% of body weight) had been reached. At the end point, mice were euthanized with carbon dioxide ($CO_2$).

Enumeration of EHEC O157 Shed in Feces

Fresh feces of mice were weighed and suspended in PBS (0.5 g of feces per 4.5 ml of 0.1% [w/v] sterile peptone water) to obtain a concentration of 100 mg ml$^{-1}$. The fecal suspensions were serially diluted 10-fold and appropriate dilutions were plated in triplicate on LB agar alone and on LB agar supplemented with 50 µg ml$^{-1}$ Amp and Km. Colonies that developed after incubation for 24 h at 37° C. were counted. The limit of detection was $10^2$ CFU g$^{-1}$ feces.

A value of $10^2$ g$^{-1}$ feces was assigned to any culture showing no detectable colonies for the purpose of statistical analysis.

Statistical Analysis

All results in this study are means of three independent trials±standard deviations. The Student's t test was used, when necessary, to assess the statistical significance of the differences between test and control groups (P<0.05).

Example 8

Effect of Enzymes, Temperature and pH on CFSM Activity

All active CFSM pH was adjusted to 6.0 with sterile 1N NaOH, Aliquots of the samples were treated with the following enzymes (1 mg ml$^{-1}$) and incubated for 2 h at 30° C.: Proteinase K (Sigma-Aldrich Ltd., Oakville, ON, Canada), trypsin (Sigma-Aldrich) and pepsin (Sigma-Aldrich). The effect of pH on the CFSM was tested by adjusting the CFSM to values ranging from 2.0 to 10.0 (at increments of one pH unit) with sterile 1N NaOH or 1N HCL, and the treated CFSM was incubated for 30 min and 2 h, respectively, at 30° C. The effect of temperature on the activity of the CFSM was tested by heating from 30° C. to 100° C., with increments of 10° C. for a period of 20 min. All treated CFSM were tested for inhibitory activity using the EHEC O157:H7 constructs and the autoinducer bioassay described previously herein.

Enzymatic, Temperature and pH Treatment of the Probiotic CFSM. Partial inactivation of inhibitory activity against EHEC O157:1-17 LEE expression and AI-2 signaling molecule production was observed after treatment of biologically active CFSM with proteinase K and pepsin (Table 6). No reduction in activity was found after treatment with trypsin (Table 6). No decrease in activity was recorded after treatment at the different temperatures (30° C., 65° C., 90° C. and 100° C.) for 20 min (Table 6). The activity remained after 2 h of incubation at different pH values (2.0, 4.0, 6.0, 7.0 8.0, 9.0 and 10.0) (Table 6). None of the CFSM had any antimicrobial activity against EHEC O157:H7, as inhibition of growth was not observed throughout this study. Although most bacteriocins are only active against gram-positive bacteria, we needed to make sure that bacteriocins were not involved in the observed effects. We incubated *L. acidophilus* at a temperature of 37° C. which is known to greatly affect bacteriocin production (Matsusaki et al., 1996). Matzusaki at al. (Matsusaki et al., 1996) demonstrated that the optimal cultivation temperature for the production of nisin Z was 30° C. Together these results eliminate the possibility that the presence of bacteriocins was responsible for the inhibitory effects on the EHEC O157:H7 strains studied Our results demonstrated that the *L. acidophilus* secreted molecules were not affected by changes in culture pH and that the molecule(s) are heat-resistant. The partial inactivation of activity observed after addition of proteinase K and pepsin suggest that they might be small molecules that could consist of short amino acid chains. Nonetheless, these results do not confirm that the active molecules are proteinaceous.

TABLE 6

Factors affecting the inhibitory activity of *L acidophilus* CFSM towards EHEC O157:H7 LEE expression and AI-2 production/uptake.

| Treatment | Cell-free spent medium activity |
| --- | --- |
| Enzymes (0.1 mg ml$^{-1}$):<br>Proteinase K, pepsin | ± |

TABLE 6-continued

Factors affecting the inhibitory activity of *L acidophilus* CFSM towards EHEC O157:H7 LEE expression and AI-2 production/uptake.

| Treatment | Cell-free spent medium activity |
| --- | --- |
| Trypsin | + |
| pH, 2.0-10.0 | + |
| Temperature, 30-100° C. (20 min) | + |

(+) *L. acidophilus* inhibitory activity
(−) No *L. acidophilus* inhibitory activity
(±) 30% *L. acidophilus* inhibitory activity Example 9

Purification of the *L. acidophilus* La-5 Secreted Peptides

Biologically active CFSM fractions were separated by fast pressure liquid chromatography (FPLC) on a Tricorn Superdex 10/300 GL column (Amersham Bioscience, Quebec, Canada) in order to collect and separate the peptides present. The running conditions established by the manufacturer were slightly modified. Briefly, one hundred microliters of CFSM fraction at a protein concentration of approximate 3.5 mg ml$^{-1}$ dissolved in 50 mM sodium phosphate buffer pH 7.0 was injected on the Superdex Peptide column connected to a FPLC pump (ThermoFinnigan A53500, ThermoInstruments Inc., Canada. Missisauga, ON) and eluted with the same buffer at a flow rate of 0.7 ml min$^{-1}$. The absorbance was recorded at 214 and 280 nm by means of a UV detector (SpectraSYSTEM, ThermoFinnigan, ThermoInstruments Inc.). The eluted peaks were pooled, freeze-dried and concentrated 10 times in 18-Ω water. The column was calibrated with α-lactalbumin standard (2.0 mg ml$^{-1}$). The calibration curve was used to determine the average molecular weight of the unknown samples. Chromatographic graphics were obtained using the Chromatography Workstation ChromQuest™. Total protein content of the collected peaks was measured as described previously (Table 7).

TABLE 7

*L. acidophilus* CFSM and biologically active fractions total protein content.

| | Total protein content (mg/ml) |
| --- | --- |
| *Lactobacillus acidophilus* CFSM | 9.7 |
| CFSM pooled fractions | 4.1 |
| Pooled fractions peptide peaks | 2.125 |
| Peak 1 | 1.75 |
| Peak 2 | ND |
| Peak 3 | 0.125 |
| Peak 4 | 0.25 |

ND Protein content not detected

Peptide samples were then desalted and concentrated onto a $C_{18}$ Vivapure® Micro spin columns (Sartorius Biotech Inc., Edgewood, N.Y., USA), and sent to the Biological Mass Spectrometry facility at the University of Guelph (Guelph, ON., Canada) for liquid chromatography-mass spectroscopy (LC-MS) and to the Advance Protein Technology Centre for Edman sequencing at the Hospital for Sick Children (Toronto, Canada).

Figure 10:
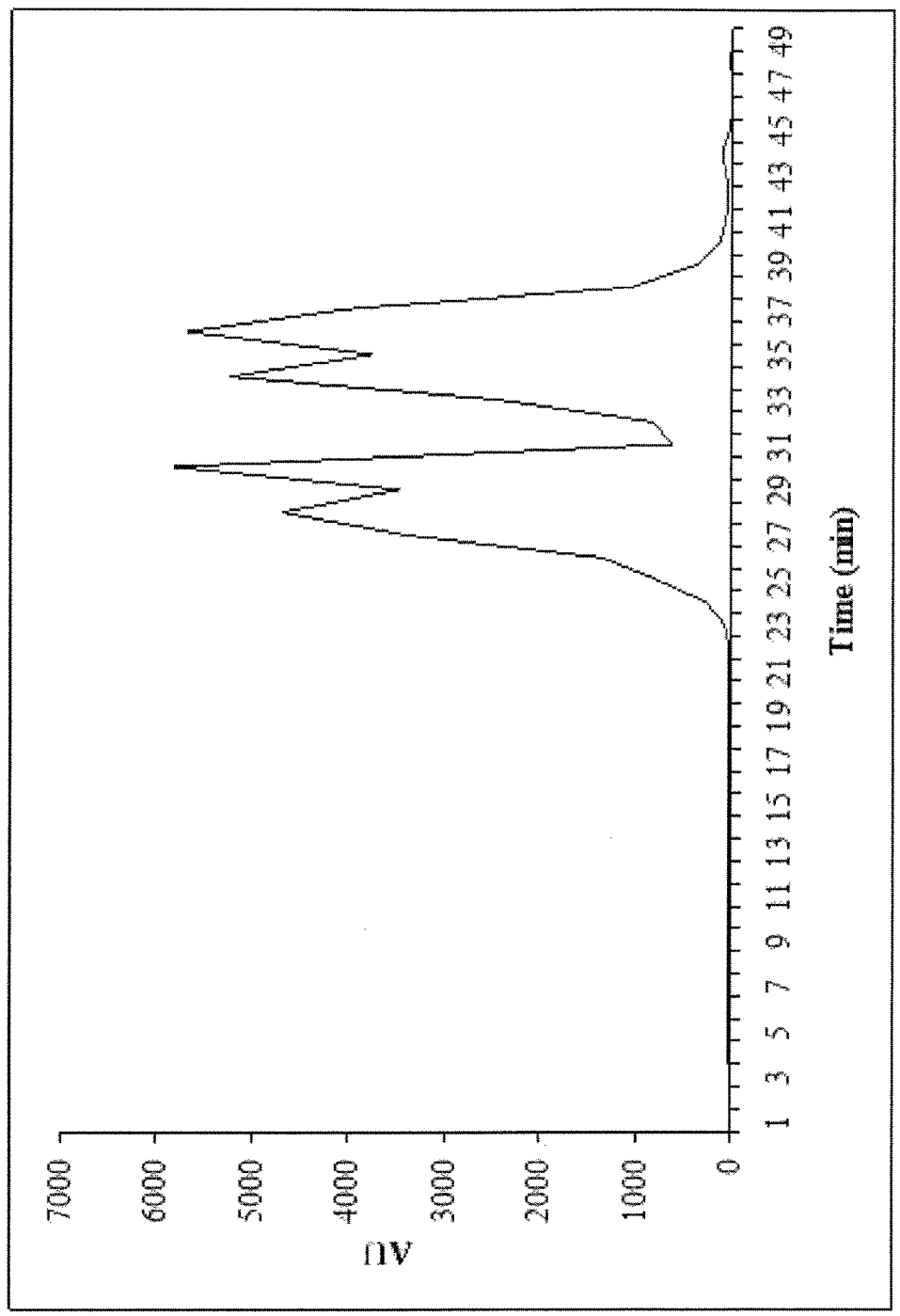
FIG. 10. Fractionation of *L. acidophilus* CFSM peptides by size exclusion FPLC.

Purification of the *L. acidophilus* La-5 Secreted Peptides. The FPLC chromatogram results show that the CFSM selected fractions are composed of four peptide fractions (FIG. 10). The molar mass of the peptide fractions was determined to be less than 14,000 Da. α-lactalbumin (MW of 14.2 kDa) was eluted at min 9.3 while the elution of the peptide peaks started at 23 min. These results demonstrate that the fractions contain small peptides that could consist of approximate 2 to 10 amino acid residues.

Figure 11:
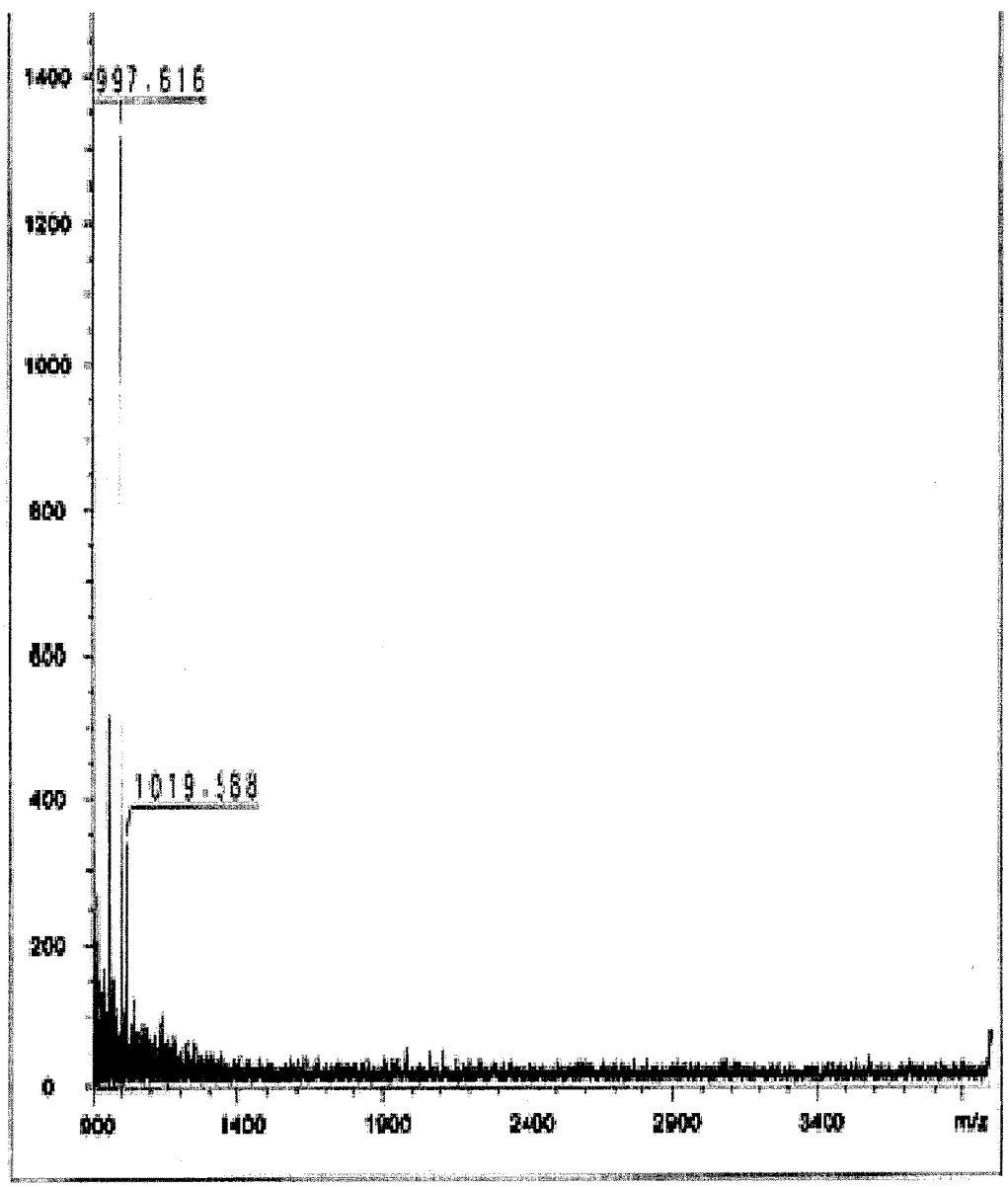
FIG. 11. LC-MS analysis of peptide peak 1 (Maira 1).
Figure 12:
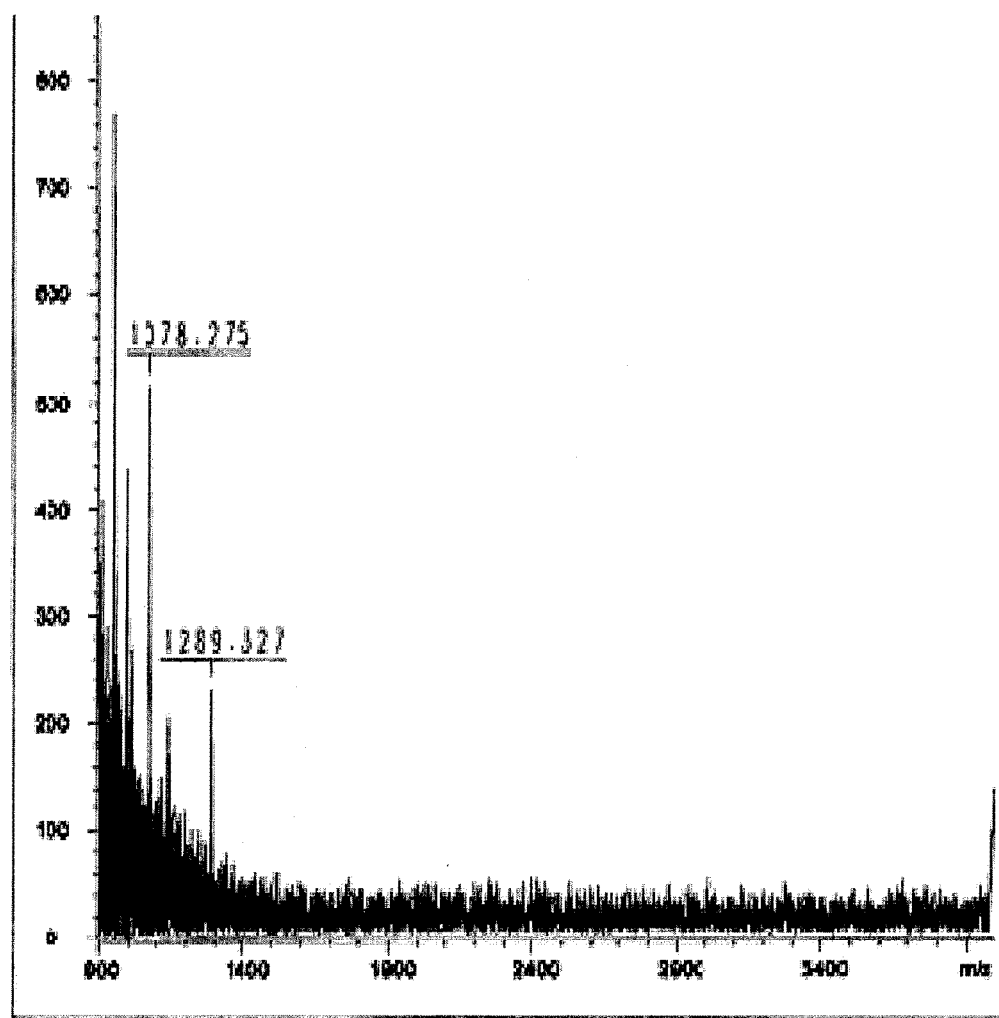
FIG. 12. LC-MS analysis of peptide peak 1 (Maira 3).
Figure 13:
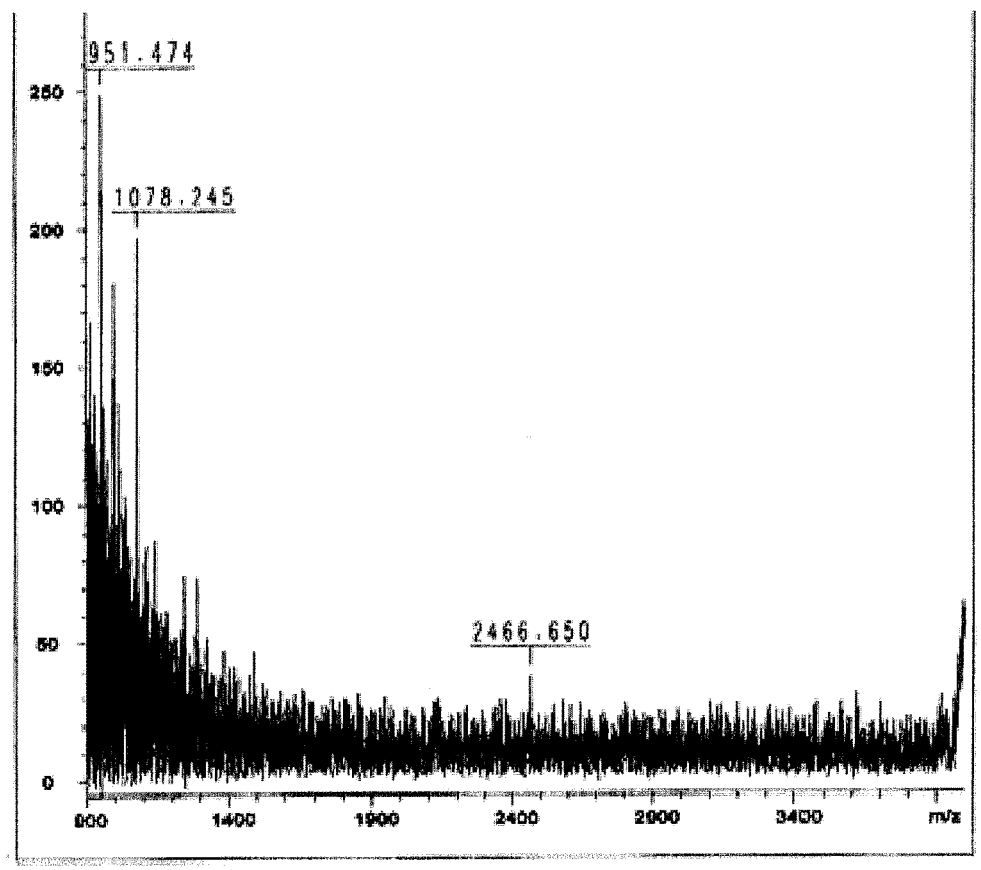
FIG. 13. LC-MS analysis of peptide peak 1 (Maira 4).
Figure 14:
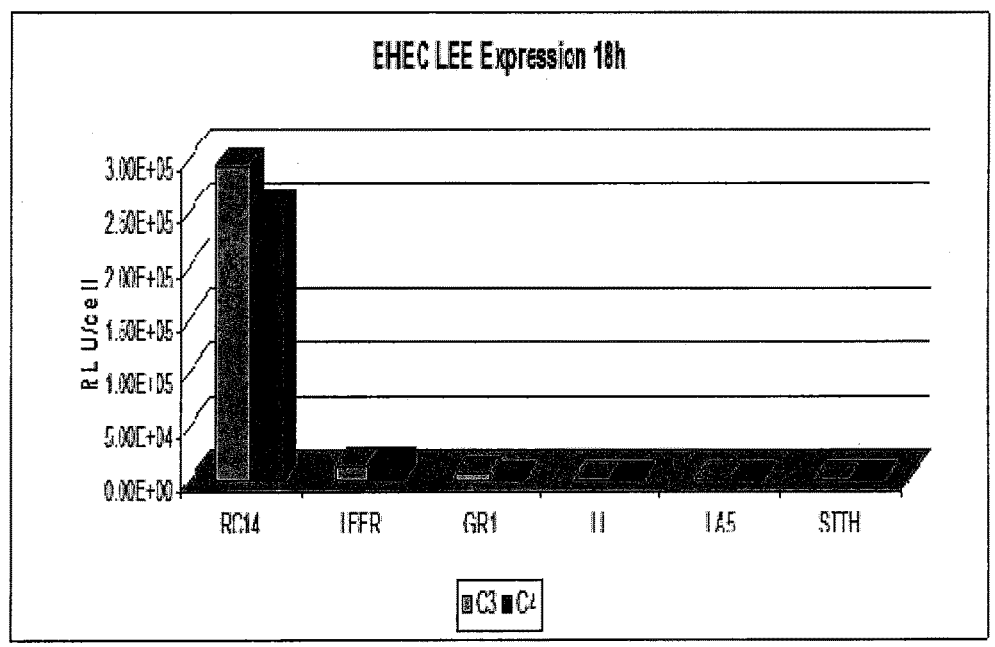
FIG. 14 *E. coli* O157:H7 construct C3 (LEE1::lux) and C4 (LEE2::lux) grown in LB broth supplemented with medium conditioned by the growth of probiotic LAB. Constructs grown in LB:MRS broth were used as positive controls (data not shown). Light induction is reported as relative light units (RLU) per cell.
Figure 15:
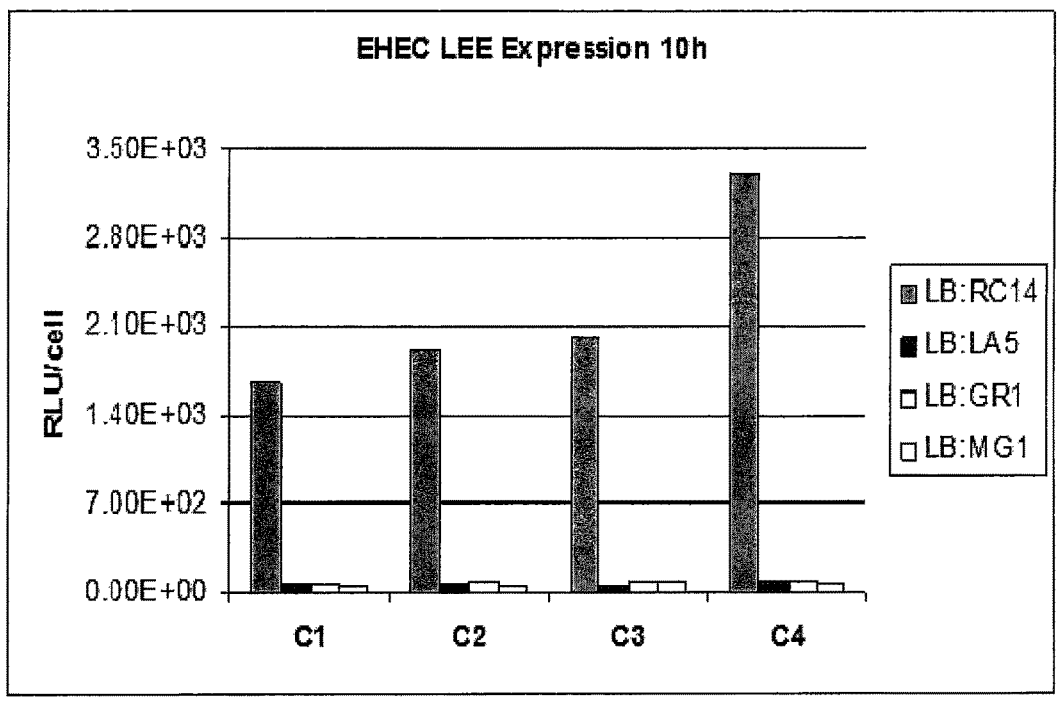
FIG. 15. *E. coli* O157:H7 construct C1 (LEE1;lux), C2 (LEE2::lux), C3 (LEE1::lux) and C4 (LEE2::lux) grown in LB broth supplemented with medium conditioned by the growth of probiotic LAB. Constructs grown in LB:MRS broth were used as positive controls (data not shown). Light induction is reported as relative light units (RLU) per cell.
Figure 16:
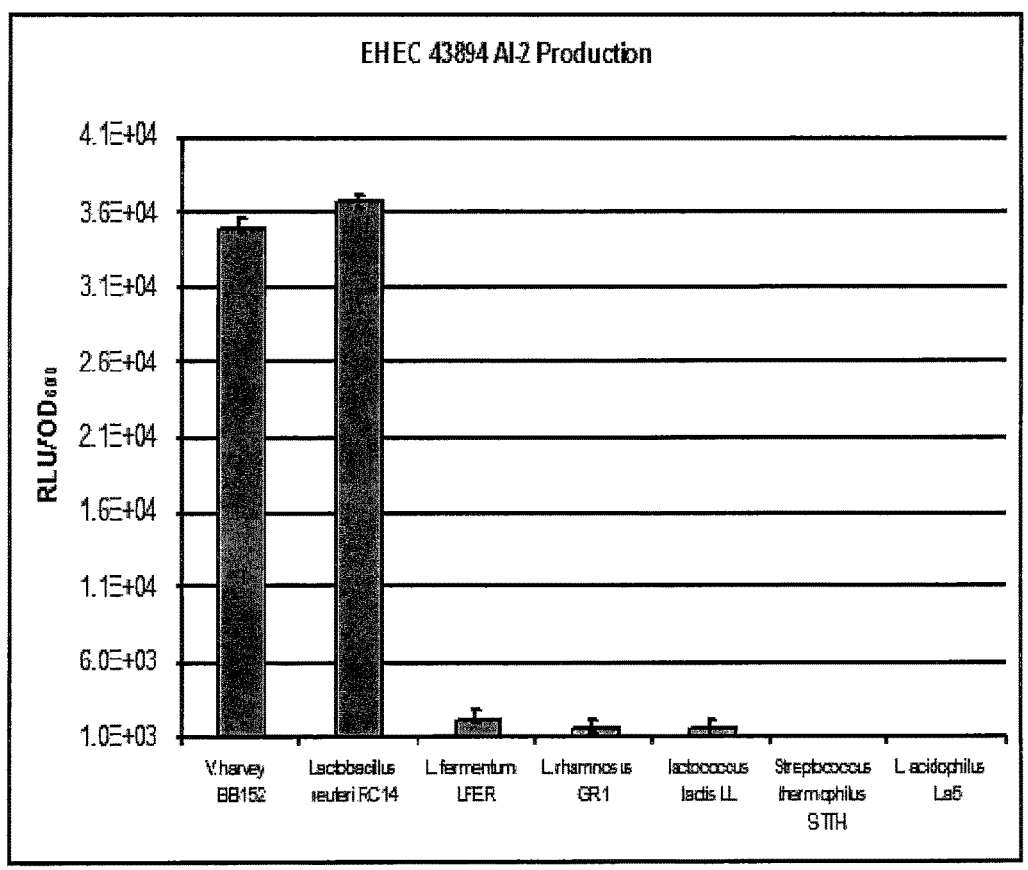
FIG. 16. AI-2 signaling molecule production as detected by the *V. harveyi* autoinducer-2 bioassay. EHEC O157:H7 strain 43894 was grown in LB broth supplemented with CFSM of probiotic LAB. Positive and negative controls were *V. harveyi* strain BB152 (+) and *E. coli* DH5α (-), respectively (negative control not shown). Results were expressed as relative light units (RLU) defined as counts min$^{-1}$ and adjusted to $OD_{600}$ (RLU/$OD_{600}$). The data are mean±SD values of three independent replicates of each sample.

Peptide peaks collected were concentrated and desalted before being sent for LC-MS analysis and peptide sequencing. Mass spectrometry was carried out using an Agilent HPLC, coupled to an Agilent 6110 single quadripole LC/MS (Agilent Technologies). The molar masses of three peptide peaks (FI, FIII and FIV) were detected at m/z 994, 997, 1019, 1078, 1139, 1289 and 2466. Peptide peak (FII) showed no signal peaks (FIGS. 11, 12 and 13). The peptide sequencing analysis of peaks FI, FII and FIV showed that the peptide fractions are composed of 4 to 6 amino acid residues (Table 8). There is a possibility that the amino acid sequences obtained are partial peptide sequences of larger peptides or small proteins due to possible blocked N-termini. Blocked N-termini provide the single largest impediment to protein sequence analysis. An estimated 50-80% of all proteins naturally have chemically modified N-termini. The sequential Edman analysis sequences the N-terminal and internal protein. In this process, the N-terminal amino acid is reacted with phenylisothiocyanate (PITC) to form a phenylthiocarbamyl (PTC) protein. The PTC protein is then cleaved with trifluoroacetic acid (TFA), resulting in the formation of an intermediate anilinothiazolinone (ATZ). The intermediate is converted to the more stable phenylthiohydantoin (PTH) amino acid derivative and subsequently separated by HPLC, compared against a standard, and identified by the sequencer software.

TABLE 8

Peptide sequencing analysis.

| Sample | Amino acid residues | | | | | |
|---|---|---|---|---|---|---|
| Peptide peak (FI) | Y-Tyr | P-Pro | V-Val | E-Glu | P-Pro | F-Phe |
| Peptide peak (FIII) | A-Ala, Y-Tir$^a$, V-Val | P-Pro | P-Pro | G-Gly, Y-Tyr | G-Gly, Y-Tyr | P-Pro |
| Peptide peak (IV) | N-Asn, A-Ala, F-Phe | Q-Gln | P-Pro | Y-Tyr | | |

$^a$Amino acid most likely to be present at residue 1

BLAST Analysis of the Peptide Sequences. The amino acid sequences of the peptide peaks were introduce in the Basic Local Alignment Search Tool (BLAST) and found a number of matches. BLASTp was done using default opening and gap penalties and a default scoring matrix. We will mention only the 100% homology (Table 9).

TABLE 9

Proteins with 100% homology to the peptide peaks as determined by BLASTp using default opening and scouring matrix and default gap penalties.

| Peak sequence/sequence aligned | BLASTp protein (100% homology to peptide sequence) |
|---|---|
| YPVEPF/YPVEPF | YP 194702 neopullulanase [*Lactobacillus acidophilus* NCFM] |
| YPPGGP/YPPG | YP 193877 ornithine decarboxylase chain A [*Lactobacillus acidophilus* NCFM] |
| NQPY/NQPY | YP 193484 glutamine ABC transporter [*Lactobacillus acidophilus* NCFM] |

Example 10

Effect of CFSM on Murine Norovirus Infection

Figure 17A:
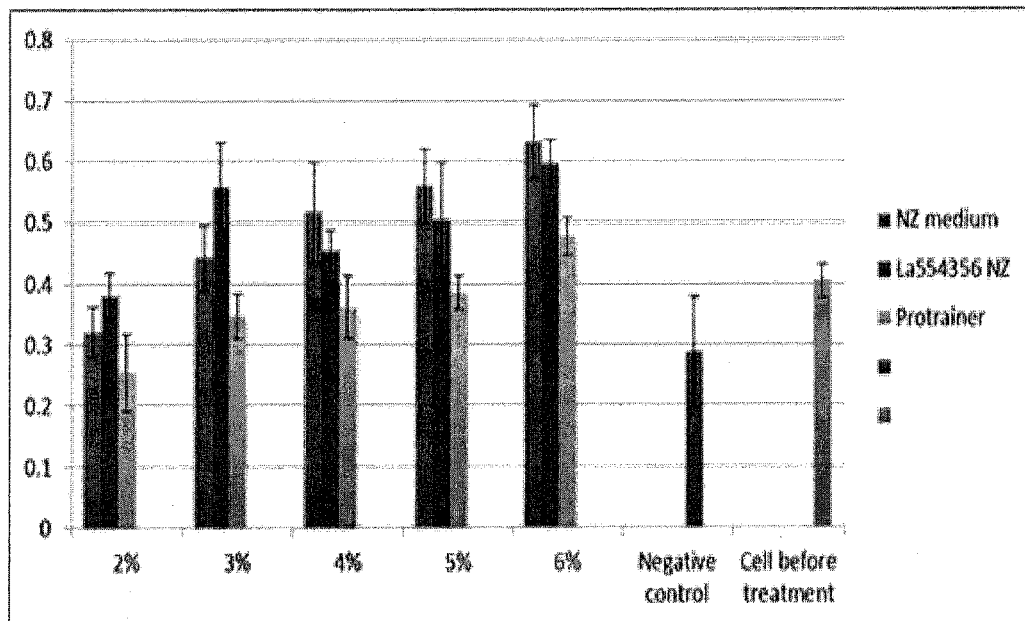
FIG. 17. (A) Effect of whey based medium alone (NZ medium) or including probiotic peptides derived from *L.*
Figure 17B:
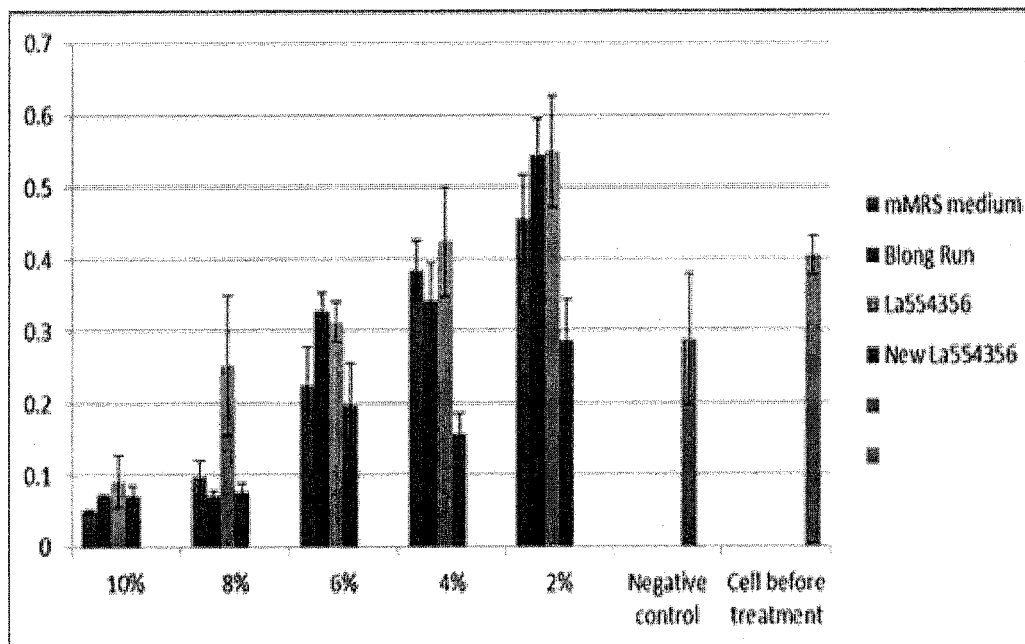

CFSM was initially applied to virus-free cell cultures to determine the concentration of CFSM that could be used on FRhK cells without itself causing any detrimental effects on the cells. In FIGS. 17A and 17B, it can be seen that 2% CFSM is a desirable amount to use and this amount was used for subsequent experiments.

Next, viral particles in infected RAW 264.7 cells and media in the presence of probiotic CFSM were quantified. Mouse macrophage RAW 264.7 cells were infected with MNV-1 at $1 \times 10^6$ cells with $3.5 \times 10^6$ PFU. After RNA extraction from cells and media (supernatant), quantification of MNV-1 particles was done by a 2-step real-time PCR. The analysis showed a statistical difference (t-test, $p<0.05$) between the amounts of viral particles present in the media (FIG. 18B) compared to untreated infected cells. For the number of viral particles inside the cells, only *Lactococcus lactis* and *Lactobacillus reuteri* (FIG. 18A), showed a statistical difference compared to infected cells, however, *Lactobacillus acidophilus* La-5 showed a trend towards statistical significance. These results show that the propagation of MNV-1 might be negatively affected by the presence of bioactive compounds produced by probiotic strains.

Example 11

Effect of CFSM on Hepatitis A Infection

Figure 19A:
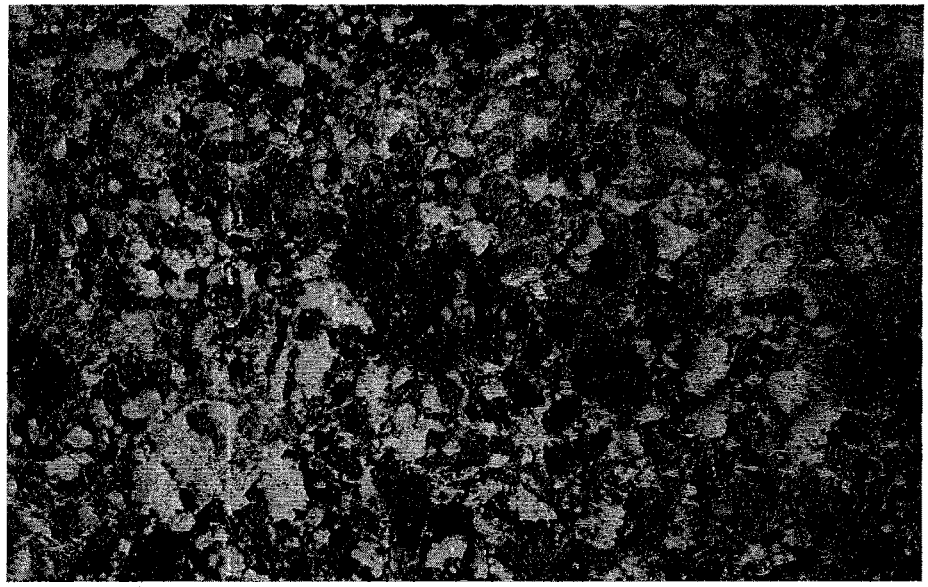
Figure 19B:
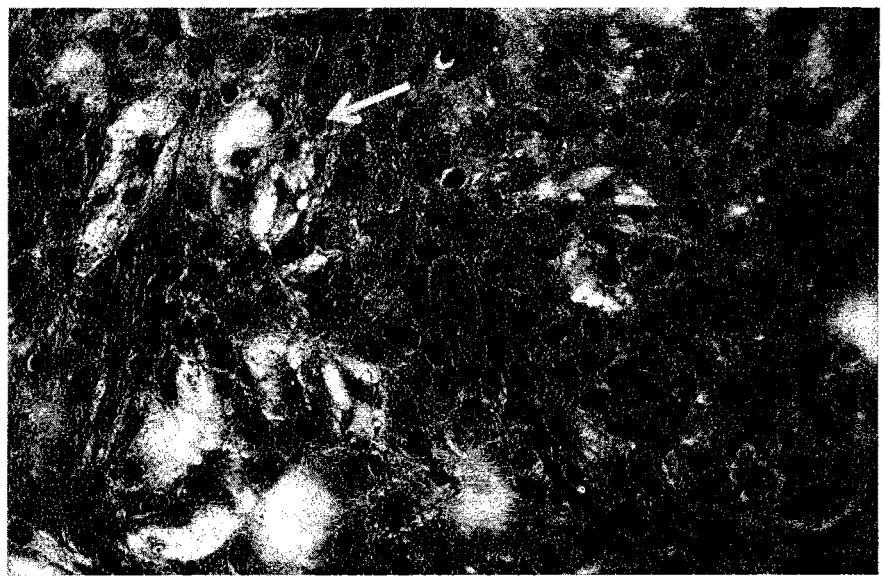
Figure 19C:
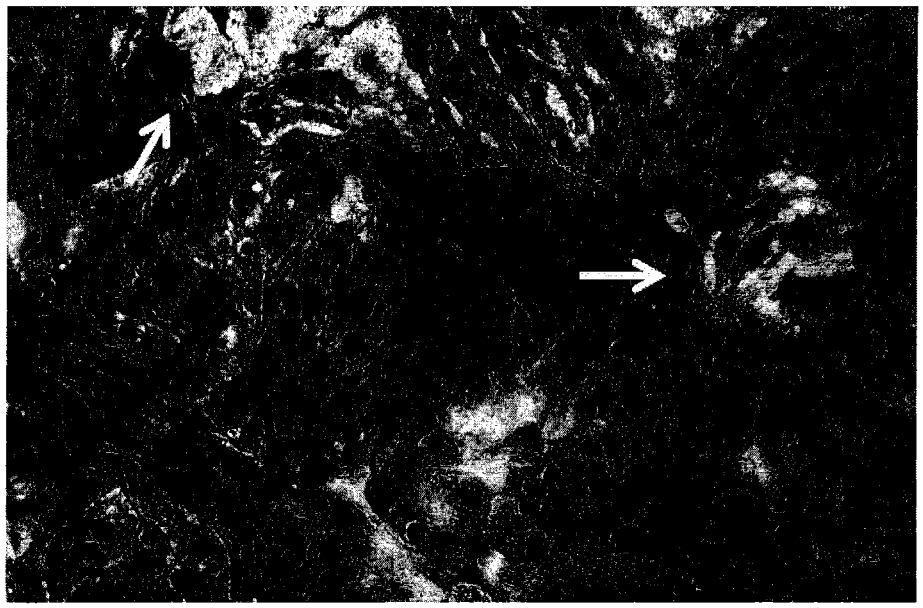
Figure 19D:
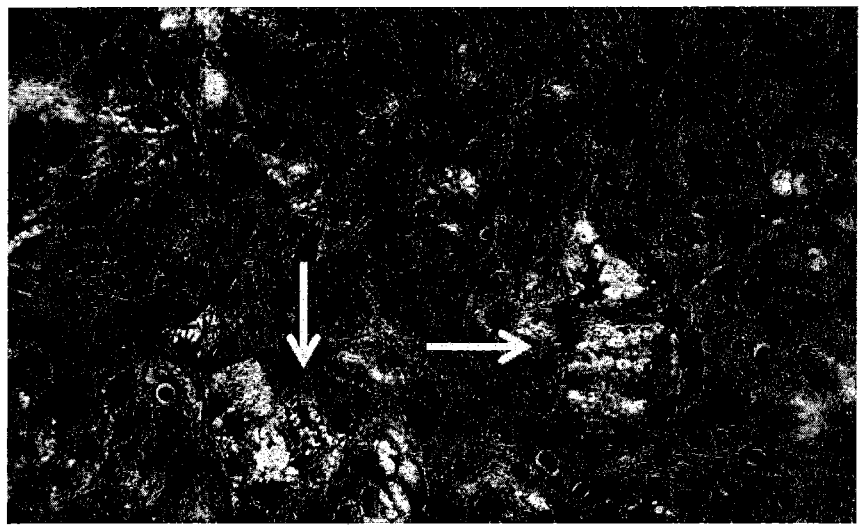

The effects of probiotic molecule-containing CFSM on cells that are infected with HAV was studied. Control cells are shown in FIG. 19A. CFSM from *Lactobacillus lactis* La-5 (FIG. 19B), *L. reuteri* (FIG. 19C), and *Lactococcus lactis* (FIG. 19D) were applied to a monolayer of cells infected with HAV and a decrease in the infection of HAV was observed. The arrows in these figures point at the infected cells and the rest of the cells comprise the uninfected monolayer.

Example 12

Evaluation of Probiotic Bioactives on the Murine Norovirus Infection in Mice

*Lactobacillus acidophilus* La5 and *Lactococcus lactis* were grown in whey protein based media. The spent medium after fermentation was freeze-dried and stored at −80 C until used. The activity of both supernatants, based on the down-regulation of the LEE::luxCDABE *E. coli* O157 construct, was evaluated using bioluminescence assay (FIG. 20).

The supernatants were used as a prophylactic treatment in immunocompromised mice to determine the protective affect against murine norovirus infection. The amount administered to each mouse was set at 0.8 mg/ml of protein (estimated by spectrophotometry) as determined in a previous dose/response study.

The challenge study comprised 3 treatments:
Group #1 (n=6): Oral gavage with 100 μl saline solution
Group #2 (n=6): Oral gavage with 100 μl of La-5 probiotic bioactive.
Group #3 (n=6): Oral gavage with 100 μl of *L. lactis* probiotic bioactive.

All groups were infected with a single dose of MNV-1 ($10^7$ PFU/mice) and assessed daily for weight loss, signs of dehydration, and diarrhea. Briefly:

1) Mice were separated in groups (n=6) upon arrival at the Isolation Unit, at the University of Guelph.
2) Rectal swabs were taken at −4, −1, 0, 1, 2, 3 and 4d to determine the shedding of viral particles.
3) Daily oral administration of probiotic bioactive (or saline for control) to mice for six days prior to infection and 3 days after infection (Day −6 to +3).
4) Blood sampling on day 0 from all groups.
5) Single oral administration by gavaging of MNV-1 at day 0
6) Euthanasia of all mice with $CO_2$ inhalation 4 days post challenge (Day 4).

The study end point was determined by the use of monitoring charts and clinical scoring. Loss of ≥20% of body weight automatically indicated an endpoint but the general body conditions (e.g., haircoat, posture) were criteria used in determining an endpoint. Mouse clinical scoring was as follows:

General Condition
0=clinically normal
1=slightly abnormal
2=moderately abnormal
3=severely abnormal Animals that were not treated with probiotic spent media showed a decrease in the general body condition at day 2 poi. Two mice from the treated-lactis group had to be euthanized at day 2. At day 3 poi, body weight loss was used as endpoint as well as clinical scoring (Tables 10 and 11). For treated groups, 50% of the animals were in a stable condition at day 3 and were kept in isolation until day 4 poi for observation. As can be seen, the weight of the mice in the two treated groups was significantly higher at the day 3 endpoint than the weight of the mice in the control group (Table 11), clinical scoring was significantly improved, mortality was reduced, and survival was increased (Table 12).

TABLE 11

Weight of mice groups at 3 days after infection.

| Group | Weight 3 d poi (g) |
|---|---|
| Untreated | 15.35 ± 0.9 |
| Treated—La5 | 16.7 ± 1.7* |
| Treated—Lactis | 17.7 ± 1.4* |

*Statistical difference t-Student, La5 P = 0.058, lactis P = 0.04 compared to untreated animals

TABLE 12

Table 2 Mortality and clinical scoring of mice after Mortality and clinical scoring of mice after infection with MNV-1

| Groups | 3 d poi | | 4 d poi |
|---|---|---|---|
| | Scoring | Mortality | Mortality |
| Untreated | 1.4 ± 1.3 | 100% | — |
| Treated—La5 | 0.9 ± 1.0* | 50% | 50% |
| Treated—Lactis | 0.38 ± 0.8* | 33%[a] | 50% |

[a]Two animals were euthanized at 2 d poi.
*Statistical difference during 3 d compared to untreated animals t-Student La5 P = 0.003, lactis P = 0.001.

The overall well-being of animals treated with probiotics was significantly better compared to the untreated animals. This seems to correlate with the levels of ALT and AST in animals that survived until the end of the trial (4d poi; Table 13). The concentration of these enzymes is an indication of liver damage and the extent of tissue damage, respectively.

TABLE 13

Alanine aminotransferase (ALT) and aspartate aminotransferase (AST) in mice after challenge with MNV-1.

| Group | 6 d probiotic tr. | End point | 4 d poi | Reduction |
|---|---|---|---|---|
| ALT (U/L) | | | | |
| Treated—La5 | 30.5 | 216 | 106 | 60% |
| Treated—lactis | 29 | 95* | 192 | 27% |
| Untreated | NA | 264 | NA | |
| AST (U/L) | | | | |
| Treated—La5 | NA | 1246 | 683 | 55% |
| Treated—lactis | 86.5 | 951* | 1316 | 13% |
| Untreated | NA | 1509 | | |

NA - short sample
*at 2 d poi
Reduction = $(AST_o - AST_F)/AST_o$

In general, the tissues from animals that survived the challenge showed less visual damaged (FIG. 21). FIGS. 21A and 21B show mice that were treated with the probiotic supernatant and survived the challenge at 3d poi, while FIG. 21C shows the untreated mice at 3d poi. As can be seen, the mice in FIGS. 21A and 21B were active while the untreated mice in FIG. 21C are hunched, not nesting and barely active. FIGS. 21D and 21E show the internal organs of mice with treated with La5 at 3d and 4d poi, respectively. Stomachs were full with feed. FIG. 21F shows a mouse from the lactis treated group euthanized at 2d poi, showing little protection against infection. FIG. 21G shows the internal organs of an untreated mouse. FIGS. 21F and 21G show the bloated stomach of mice that did not present with a beneficial effect. FIGS. 21H and 21I are images of lactis treated mice and La5 treated mice at the end of the trial.

The viral load in the jejunum and cecum of the mice was determined using a 2step RT-qPCR, which was optimized ($y=-3.3993x+39.254$, $R^2=0.99$) using a High Capacity cDNA kit (4368814 Applied Biosystems), PowerSYBR-green 2× (part#4367659, Life Technologies) and MNV-1 RNA as template. Primers used were MGmurine primers (F1-gctgcggcctctcttgac, R2-agggatggtgtcctgaaaacc) at 300 nM with an annealing temperature=60° C. in a ViiA7 real-time PCR system (Applied Biosystems). Tissues were weighed and resuspended in 200 μl PBS before homogenization with a disposable pestle (Fisher Scientific), The homogenate was used for RNA extraction following the QIAamp Viral RNA Mini Kit instructions (Qiagen Inc.). Following this procedure, MNV-1 was not detected in the jejunum of euthanized animals of group La5 at 3d poi. Although the virus was detected in two animals of the La5 group that survived (Table 14), the amounts were considerably lower compared to the control. MNV-1 was detected in the cecum of all the groups; however, there was a significantly lower concentration of virus in the mice that survived the challenge (Table 14).

TABLE 14

Presence of MNV-1 in the intestine of immmunocompromised mice

| Group | Jejunum | | Cecum | |
|---|---|---|---|---|
| | Freq. | PFU/g | Freq. | PFU/g |
| Untreated | 4/6 | $8.3 \times 10^4 \pm 1.23 \times 10^5$ | 6/6 | $4.31 \times 10^5 \pm 3.42 \times 10^5$ |

TABLE 14-continued

Presence of MNV-1 in the intestine of immmunocompromised mice

| Group | Jejunum | | Cecum | |
|---|---|---|---|---|
| | Freq. | PFU/g | Freq. | PFU/g |
| Treated—La5 | 2/6 | 1.06 | 6/6 | *1.83 × $10^4$ ± 2.31 × $10^4$ |
| Treated—lactis | 1/6 | 25 | 6/6 | *1.18 × $10^5$ ± 2.31 × $10^5$ |

*p = 0.03 and 0.014 for La5 and lactis treatments, respectively.

These results showed the significant beneficial effect of probiotic spent media in the treatment of norovirus infection. The prophylactic effect of the bioactives produced by Lactobacillus acidophilus La5 and Lactococcus lactis after fermentation in a whey protein based media could potentially be enhanced when pure fractions are used. Considering mortality, weight loss, clinical scoring, blood biochemistry and viral load in tissues, the treatments showed a significant effect on the protection against norovirus infection in immunocompromised mice.

REFERENCES 1. 1993. Guide to the care and use of experimental animals. In C. C. o. A. Care (ed.), 2nd Edition ed, vol. 1 & 2.
2. Asahara, T., K. Shimizu, K. Nomoto, T. Hamabata, A. Ozawa, and Y. Takeda. 2004. Probiotic bifidobacteria protect mice from lethal infection with Shiga toxin-producing Escherichia coli O157:H7. Infect Immun 72:2240-7.
3. Beinke, C., S. Laarmann, C. Wachter, H. Karch, L. Greune, and M. A. Schmidt. 1998. Diffusely adhering Escherichia coli strains induce attaching and effacing phenotypes and secrete homologs of Esp proteins. Infect Immun 66:528-39.
4. Brovko, L. Y., C. Vandenende, B. Chu, K. Y. Ng, A. Brooks, and M. W. Griffiths. 2003. In vivo assessment of effect of fermented milk diet on course of infection in mice with bioluminescent Salmonella. J Food Prot 66:2160-3.
5. Clarke, M. B., and V. Sperandio. 2003. Presented at the 103rd American Society for Microbiology General Meeting, Washington, D.C., USA, May 18-22, 2003^_20030518.
6. Costa-Carvalho, B. T., A. Bertipaglia, D. Sole, C. K. Naspitz, and I. C. Scaletsky. 1994. Detection of immunoglobulin (IgG and IgA) anti-outer-membrane proteins of enteropathogenic Escherichia coli (EPEC) in saliva, colostrum, breast milk, serum, cord blood and amniotic fluid. Study of inhibition of localized adherence of EPEC to HeLa cells. Acta Paediatr 83:870-3.
7. Cravioto, A., A. Tello, H. Villafan, J. Ruiz, S. del Vedovo, and J. R. Neeser. 1991. Inhibition of localized adhesion of enteropathogenic Escherichia coli to HEp-2 cells by immunoglobulin and oligosaccharide fractions of human colostrum and breast milk. J Infect Dis 163:1247-55.
8. Donnenberg, M. S., J. B. Kaper, and B. B. Finlay. 1997. Interactions between enteropathogenic Escherichia coli and host epithelial cells. Trends Microbiol 5:109-14.
9. Donnenberg, M. S., C. O. Tacket, S. P. James, G. Losonsky, J. P. Nataro, S. S. Wasserman, J. B. Kaper, and M. M. Levine. 1993. Role of the eaeA gene in experimental enteropathogenic Escherichia coli infection. J Clin Invest 92:1412-7.
10. Donnenberg, M. S., J. Yu, and J. B. Kaper. 1993. A second chromosomal gene necessary for intimate attachment of enteropathogenic Escherichia coli to epithelial cells. J Bacteriol 175:4670-80.
11. Gagnon, M., E. E. Kheadr, N. Dabour, D. Richard, and I. Fliss. 2006. Effect of Bifidobacterium thermacidophilum probiotic feeding on enterohemorrhagic Escherichia coli O157:H7 infection in BALB/c mice. Int J Food Microbiol 111:26-33.
12. Gansheroff, L. J., M. R. Wachtel, and A. D. O'Brien. 1999. Decreased adherence of enterohemorrhagic Escherichia coli to HEp-2 cells in the presence of antibodies that recognize the C-terminal region of intimin. Infect Immun 67:6409-17.
13. Gill, H. S., Q. Shu, H. Lin, K. J. Rutherfurd, and M. L. Cross. 2001. Protection against translocating Salmonella typhimurium infection in mice by feeding the immuno-enhancing probiotic Lactobacillus rhamnosus strain HN001. Med Microbiol Immunol 190:97-104.
14. Huebner, E. S., and C. M. Surawicz. 2006. Probiotics in the prevention and treatment of gastrointestinal infections. Gastroenterol Clin North Am 35:355-65.
15. Hutt, P., J. Shchepetova, K. Loivukene, T. Kullisaar, and M. Mikelsaar. 2006. Antagonistic activity of probiotic lactobacilli and bifidobacteria against entero- and uropathogens. J Appl Microbiol 100:1324-32.
16. Imase, K., A. Tanaka, K. Tokunaga, H. Sugano, H. Ishida, and S. Takahashi, 2007. Lactobacillus reuteri tablets suppress Helicobacter pylori infection—a double-blind randomised placebo-controlled cross-over clinical study. Kansenshogaku Zasshi 81:387-93.
17. Jarvis, K. G., J. A. Giron, A. E. Jerse, T. K. McDaniel, M. S. Donnenberg, and J. B. Kaper. 1995. Enteropathogenic Escherichia coli contains a putative type III secretion system necessary for the export of proteins involved in attaching and effacing lesion formation. Proc Natl Acad Sci USA 92:7996-8000.
18. Jarvis, K. G., and J. B. Kaper. 1996. Secretion of extracellular proteins by enterohemorrhagic Escherichia coli via a putative type III secretion system. Infect Immun 64:4826-9.
19. Jerse, A. E., J. Yu, B. D. Tall, and J. B. Kaper. 1990. A genetic locus of enteropathogenic Escherichia coli necessary for the production of attaching and effacing lesions on tissue culture cells. Proc Natl Acad Sci USA 87:7839-43.
20. Kendall, M. M., and V. Sperandio. 2007. Quorum sensing by enteric pathogens. Curr Opin Gastroenterol 23:10-5.
21. Kenny, B., and B. B. Finlay. 1995. Protein secretion by enteropathogenic Escherichia coli is essential for transducing signals to epithelial cells. Proc Natl Acad Sci USA 92:7991-5.
22. Knutton, S., T. Baldwin, P. H. Williams, and A. S. McNeish. 1989. Actin accumulation at sites of bacterial adhesion to tissue culture cells: basis of a new diagnostic test for enteropathogenic and enterohemorrhagic Escherichia coli. Infect Immun 57:1290-8.
23. Knutton, S., R. K. Shaw, R. P. Anantha, M. S. Donnenberg, and A. A. Zorgani. 1999. The type IV bundle-forming pilus of enteropathogenic Escherichia coli undergoes dramatic alterations in structure associated with bacterial adherence, aggregation and dispersal. Mol Microbiol 33:499-509.
24. Lai, L. C., L. A. Wainwright, K. D. Stone, and M. S. Donnenberg. 1997. A third secreted protein that is encoded by the enteropathogenic Escherichia coli pathogenicity island is required for transduction of signals and for attaching and effacing activities in host cells. Infect Immun 65:2211-7.

25. Mayville, P., G. Ji, R. Beavis, H. Yang, M. Goger, R. P. Novick, and T. W. Muir. 1999. Structure-activity analysis of synthetic autoinducing thiolactone peptides from *Staphylococcus aureus* responsible for virulence. Proc Natl Acad Sci USA 96:1218-23.

26. McKee, M. L., A. R. Melton-Celsa, R. A. Moxley, D. H. Francis, and A. D. O'Brien. 1995. Enterohemorrhagic *Escherichia coli* O157:H7 requires intimin to colonize the gnotobiotic pig intestine and to adhere to HEp-2 cells. Infect Immun 63:3739-44.

27. McKee, M. L., and A. D. O'Brien. 1995. Investigation of enterohemorrhagic *Escherichia coli* O157:H7 adherence characteristics and invasion potential reveals a new attachment pattern shared by intestinal *E. coli*. Infect Immun 63:2070-4.

28. McKee, M. L., and A. D. O'Brien. 1996. Truncated enterohemorrhagic *Escherichia coli* (EHEC) O157:H7 intimin (EaeA) fusion proteins promote adherence of EHEC strains to HEp-2 cells. Infect Immun 64:2225-33.

29. Medellin-Pena, M. J., H. Wang, R. Johnson, S. Anand, and M. W. Griffiths. 2007. Probiotics affect virulence-related gene expression in *Escherichia coli* O157:H7. Appl Environ Microbiol 73:4259-67.

30. Novak, J., and J. A. Katz. 2006. Probiotics and prebiotics for gastrointestinal infections. Curr Infect Dis Rep 8:103-9.

31. Shu, Q., and H. S. Gill. 2001. A dietary probiotic (*Bifidobacterium lactis* HN019) reduces the severity of *Escherichia coli* O157:H7 infection in mice. Med Microbiol Immunol 189:147-52.

32. Shu, Q., and H. S. Gill. 2002. Immune protection mediated by the probiotic *Lactobacillus rhamnosus* HN001 (DR20) against *Escherichia coli* O157:H7 infection in mice. FEMS Immunol Med Microbiol 34:59-64.

33. Snelling, A. M. 2005. Effects of probiotics on the gastrointestinal tract. Curr Opin Infect Dis 18:420-6.

34. Sperandio, V., J. L. Mellies, W. Nguyen, S. Shin, and J. B. Kaper. 1999. Quorum sensing controls expression of the type III secretion gene transcription and protein secretion in enterohemorrhagic and enteropathogenic *Escherichia coli*. Proceedings of the National Academy of Science, USA 96:15196-15201.

35. Sperandio, V., A. G. Torres, J. A. Girón, and J. B. Kaper. 2001. Quorum sensing is a global regulatory mechanism in enterohemorrhagic *Escherichia coli* O157:H7. Journal of Bacteriology 183:5187-5197.

36. Sperandio, V., A. G. Torres, B. Jarvis, J. P. Nataro, and J. B. Kaper. 2003. Bacteria-host communication: The language of hormones. Proceedings of the National Academy of Science, USA 100:8951-8956.

37. Tzipori, S., F. Gunzer, M. S. Donnenberg, L. de Montigny, J. B. Kaper, and A. Donohue-Rolfe. 1995. The role of the eaeA gene in diarrhea and neurological complications in a gnotobiotic piglet model of enterohemorrhagic *Escherichia coli* infection. Infect Immun 63:3621-7.

38. Vinderola, G., C. Matar, and G. Perdigon. 2007. Milk fermented by *Lactobacillus helveticus* R389 and its non-bacterial fraction confer enhanced protection against *Salmonella enteritidis* serovar Typhimurium infection in mice. Immunobiology 212:107-18.

39. Bajaj, V., Lucas, R. L., Hwnag, C., and Lee, C. A. (1996) Co-ordinate Regulation of *Salmonella typhymurium* Invasion Genes by Environmental and Regulatory Factors is Mediated by Control of hilA Expression. *Molecular Microbiology* 22: 703-714.

40. Behlau, I., and Miller, S. I. (1993) A PhoP-repressed Gene Promotes *Salmonella typhimurium* Invasion of Epithelial Cells. *Journal of Bacteriology* 175: 4475-4484.

41. Chen, L., Kaniga, K., and Galan, J. (1996) *Salmonella* spp. are cytotoxic for cultured macrophages. *Molecular Microbiology* 21: 1101-1115.

43. Hueck, C. J. (1998) Type III Protein Secretion Systems in Bacterial Pathogenes of Animals and Plants. *Microbiology and Molecular Biology Reviews* 62: 379-433.

44. Kubori, T., Matsushima, Y., Nakamura, D., Uralil, J., Lara-Tejero, M., Sukhan, A., Galan, J., and Aizawa, S. (1998) Supramolecular structure of the *Salmonella typhimurium* Type III Protein Secretion System. *Science* 280: 602-605.

45. Lee, C. A., and Falkow, S. (1990) The Ability of *Salmonella* to Enter Mammalian Cells is Affected by Bacterial Growth State. *Proceedings of the National Academy of Sciences* 87: 4304-4308.

46. Lindgren, S. W., Stojiljkovic, I., and Heffron, F. (1996) Macrophage Killing is an Essential Virulence Mechanism of *Salmonella typhimurium*. *Microbiology and Molecular Biology Reviews* 93: 4197-4201.

47. Monack, D. M., Raupach, B., Hromockyj, A. E., and Falkow, S. (1996) *Salmonella typhimurium* Invasion induces apoptosis in Infected Macrophages. *Microbiology and Molecular Biology Reviews* 93: 9833-9838.

48. (Threlfall, E. J. et al., Vet. Rec. 134:577 (1994).

49. Holzapfel W H, et al. Int J Food Microbiol 1998 May 26; 41(2): 85-101.

50. von Wright, et al. Eur J Gastroenterol Hepatol 1999 November; 11(11): 1195-119.

51. Marteau, P R et al. Am J Clin Nutr February; 73(2 Suppl): 430S-436S.

52. Cummings J H, et al. Am J Clin Nutr 2001 February; 73(2 Suppl): 415S-420S.

The invention claimed is:

1. A method for reducing incidence and/or for treatment of a Noroviris infection in mammals, the method comprising administering an effective amount of a composition comprising molecules secreted by probiotic bacteria selected from the group consisting of *Lactobacillus, Lactococcus, Streptococcus, Bifidobacterium*, and combinations thereof, wherein the secreted molecules are peptides having from 2 to 10 amino acids.

2. The method of claim 1, wherein said probiotic bacteria is selected from the group consisting of *Lactobacillus acidophilus, Lactobacillus reuteria, Lactococcus lactis*, and combinations thereof.

3. The method of claim 2, wherein said *Lactobacillus acidophilus* is strain La-5.

4. The method of claim 1, wherein said *Lactobacillus* is selected from the group consisting of *Lactobacillus acidophilus , Lactobacillus fermentum, Lactobacillus rhamnosus, Lactobacillus reuteri, Lactobacillus helveticus*, and *Lactobacillus plantarum*.

5. The method of claim 1, wherein said *Lactococcus* is *Lactococcus lactis*.

6. The method of claim 1, wherein said *Bifidobacterium* is selected from the group consisting of *Bifidobacterium longum, Bifidobacterium bifidum, Bifidobacterium infantis, Bifidobacterium crudilactis*, and mixtures thereof.

7. The method of claim 1, wherein said *Streptococcus* is *Streptococcus thermophilus*.

8. The method of claim 1, wherein the composition is combined within an edible food product, nutritional supplement and/or ingestible liquid.

9. The method of claim 1, wherein the composition further comprises one or more strains of whole probiotic bacteria.

10. The method of claim 1, wherein said secreted molecule is from *Lactobacillus acidophilus*.

11. The method of claim 10, wherein said secreted molecule comprises a sequence selected from the group consisting of YPVEPF, YPPGGP, YPPG, NQPY, and combinations thereof.

12. The method of claim 1, wherein the composition further comprises a sugar source.

13. The method of claim 12, wherein the sugar source is glucose.

14. The method of claim 1, further comprising administering one or more antivirals.

15. The method of claim 1, wherein said composition is provided as a lyophilized culture fraction.

16. The method of claim 1, wherein said molecules have one or more of the following characteristics: are proteinaceous; low molecular weight; and can withstand heating at up to about 90° C., freezing, thawing, lyophilization and/or spray drying.

17. The method of claim 1, wherein the composition is a cell-free supernatant.

18. The method of claim 1, wherein the composition comprises live probiotic bacteria from which the molecules are secreted.

19. The method of claim 1, wherein the composition comprises live probiotic bacteria other than the bacteria from which the molecules are secreted.

20. The method of claim 1, wherein the molecules in the composition are purified.

21. A method for reducing incidence and/or treating infections by Norovirus in a mammal, the method comprising administering to said mammal an effective amount of a composition comprising one or more molecules secreted from a probiotic bacterium selected from the group consisting of *Lactobacillus acidophilus, Lactobacillus fermentum, Lactobacillus rhamnosus, Lactobacillus helveticus, Lactobacillus plantarum, Lactobacillus reuteri, Lactococcus lactis, Streptococcus thermophilus, Bifidobacterium longum, Bifidobacterium bifidum, Bifidobacterium infantis, Bifidobacterium crudilactis, Streptococcus thermophilus*, and combinations thereof wherein the secreted molecules are peptides having from 2 to 10 amino acids.

22. The method of claim 21, wherein said secreted molecule comprises an amino acid sequence selected from the group consisting of YPVEPF, YPPGGP, YPPG, NQPY, and combinations thereof.

23. The method of claim 21, wherein said method further comprises the administration of an antiviral.

24. A method for reducing the carriage by a food production animal of Norovirus strains that cause human infection, said method comprising administering an effective amount of one or more secreted molecules from a probiotic bacterium selected from the group consisting of *Lactobacillus acidophilus, Lactobacillus fermentum, Lactobacillus rhamnosus, Lactobacillus helveticus, Lactobacillus plantarum, Lactobacillus reuteri, Lactococcus lactis, Streptococcus thermophilus, Bifidobacterium longum, Bifidobacterium bifidum, Bifidobacterium infantis, Bifidobacterium crudilactis, Streptococcus thermophilus*, and combinations thereof to the food production animal prior to exposure to the Norovirus strains that cause human infection wherein the secreted molecules are peptides having from 2 to 10 amino acids.

* * * * *

UNITED STATES PATENT AND TRADEMARK OFFICE
CERTIFICATE OF CORRECTION

PATENT NO. : 9,861,666 B2
APPLICATION NO. : 14/457916
DATED : January 9, 2018
INVENTOR(S) : Mansel Griffiths Page 1 of 1

It is certified that error appears in the above-identified patent and that said Letters Patent is hereby corrected as shown below:

In the Specification

Column 7, Line 5: Please correct ".c" to read -- on --

Column 23, Line 30: Please correct "1-17" to read -- H7 --

Signed and Sealed this
Fifth Day of June, 2018

Andrei Iancu
*Director of the United States Patent and Trademark Office*